(12) United States Patent
Coe et al.

(10) Patent No.: US 8,317,806 B2
(45) Date of Patent: Nov. 27, 2012

(54) ENDOSCOPIC SUTURING TENSION CONTROLLING AND INDICATION DEVICES

(75) Inventors: Jonathan A. Coe, Denver, CO (US); Michael S. Cropper, Edgewood, KY (US); Richard F. Schwemberger, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 632 days.

(21) Appl. No.: 12/129,784

(22) Filed: May 30, 2008

(65) Prior Publication Data
US 2009/0299409 A1    Dec. 3, 2009

(51) Int. Cl.
    *A61B 17/04* (2006.01)
(52) U.S. Cl. ........................................... 606/148
(58) Field of Classification Search ........... 606/139, 606/144–150, 103, 213, 215, 216; 66/160, 66/213; 112/97, 470.29; 139/103, 109, 311; 140/123, 123.5
See application file for complete search history.

(56) References Cited

U.S. PATENT DOCUMENTS

| | | | |
|---|---|---|---|
| 645,576 A | 3/1900 | Telsa | |
| 649,621 A | 5/1900 | Tesla | |
| 787,412 A | 4/1905 | Tesla | |
| 1,127,948 A | 2/1915 | Wappler | |
| 1,482,653 A | 2/1924 | Lilly | |
| 1,625,602 A * | 4/1927 | Gould et al. | 606/139 |
| 2,028,635 A | 1/1936 | Wappler | |
| 2,113,246 A | 4/1938 | Wappler | |
| 2,155,365 A | 4/1939 | Rankin | |
| 2,191,858 A | 2/1940 | Moore | |
| 2,196,620 A | 4/1940 | Attarian | |
| 2,388,137 A | 10/1945 | Graumlich | |
| 2,493,108 A | 1/1950 | Casey, Jr. | |
| 2,504,152 A | 4/1950 | Riker et al. | |
| 2,938,382 A | 5/1960 | De Graaf | |
| 2,952,206 A | 9/1960 | Becksted | |
| 3,069,195 A | 12/1962 | Buck | |
| 3,170,471 A | 2/1965 | Schnitzer | |
| 3,435,824 A | 4/1969 | Gamponia | |
| 3,470,876 A | 10/1969 | Barchilon | |
| 3,669,487 A | 6/1972 | Roberts et al. | |
| 3,746,881 A | 7/1973 | Fitch et al. | |
| 3,799,672 A | 3/1974 | Vurek | |

(Continued)

FOREIGN PATENT DOCUMENTS

AU    666310 B2    2/1996

(Continued)

OTHER PUBLICATIONS

U.S. Appl. No. 11/744,271, filed May 4, 2007.

(Continued)

*Primary Examiner* — Melanie Tyson

(57) ABSTRACT

Various exemplary methods and devices are provided for tensioning sutures. The methods and devices are particularly useful in surgical suturing applications in which it is desirable to maintain tension on a suture being delivered. In various embodiments, the device is incorporated into the handle of a suture device configured to deliver a suture to a surgical site. Other embodiments comprise a device that is separate from, but may be used in connection with, a suture device configured to deliver a suture to a surgical site. A suture locking device is also provided which enables the surgeon to ascertain when a desired amount of tension has been applied to a suture prior to affixing, knotting, or tying elements thereto.

14 Claims, 13 Drawing Sheets

U.S. PATENT DOCUMENTS

| | | |
|---|---|---|
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,164,225 A | 8/1979 | Johnson et al. |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,960,133 A | 10/1990 | Hewson |
| 4,977,887 A | 12/1990 | Gouda |
| 4,984,581 A | 1/1991 | Stice |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,320,636 A | 6/1994 | Slater |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,499 A | 8/1995 | Fritzsch |
| 5,449,021 A | 9/1995 | Chikama |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |

| Patent | Date | Inventor |
|---|---|---|
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,527,321 A | 6/1996 | Hinchliffe |
| 5,540,648 A | 7/1996 | Yoon |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A | 3/1997 | Edwards et al. |
| 5,607,450 A | 3/1997 | Zvenyatsky et al. |
| 5,613,975 A | 3/1997 | Christy |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,649,372 A | 7/1997 | Souza |
| 5,653,677 A | 8/1997 | Okada et al. |
| 5,653,722 A | 8/1997 | Kieturakis |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,716,326 A | 2/1998 | Dannan |
| 5,730,740 A | 3/1998 | Wales et al. |
| 5,741,278 A | 4/1998 | Stevens |
| 5,741,285 A | 4/1998 | McBrayer et al. |
| 5,746,759 A | 5/1998 | Meade et al. |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,827,281 A | 10/1998 | Levin |
| 5,827,299 A | 10/1998 | Thomason et al. |
| 5,830,231 A | 11/1998 | Geiges, Jr. |
| 5,833,700 A | 11/1998 | Fogelberg et al. |
| 5,833,703 A | 11/1998 | Manushakian |
| 5,843,017 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,899,919 A | 5/1999 | Eubanks, Jr. et al. |
| 5,902,254 A | 5/1999 | Magram |
| 5,904,702 A | 5/1999 | Ek et al. |
| 5,908,420 A | 6/1999 | Parins et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,944,718 A | 8/1999 | Austin et al. |
| 5,951,549 A | 9/1999 | Richardson et al. |
| 5,954,720 A | 9/1999 | Wilson et al. |
| 5,954,731 A | 9/1999 | Yoon |
| 5,957,943 A | 9/1999 | Vaitekunas |
| 5,957,953 A | 9/1999 | DiPoto et al. |
| 5,971,995 A | 10/1999 | Rousseau |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |

| | | | |
|---|---|---|---|
| 5,989,182 A | 11/1999 | Hori et al. | |
| 5,993,447 A | 11/1999 | Blewett et al. | |
| 5,997,555 A | 12/1999 | Kontos | |
| 6,001,120 A | 12/1999 | Levin | |
| 6,004,269 A | 12/1999 | Crowley et al. | |
| 6,004,330 A | 12/1999 | Middleman et al. | |
| 6,007,566 A | 12/1999 | Wenstrom, Jr. | |
| 6,010,515 A | 1/2000 | Swain et al. | |
| 6,012,494 A | 1/2000 | Balazs | |
| 6,019,770 A | 2/2000 | Christoudias | |
| 6,024,708 A | 2/2000 | Bales et al. | |
| 6,024,747 A | 2/2000 | Kontos | |
| 6,027,522 A | 2/2000 | Palmer | |
| 6,030,365 A | 2/2000 | Laufer | |
| 6,033,399 A | 3/2000 | Gines | |
| 6,053,927 A | 4/2000 | Hamas | |
| 6,066,160 A | 5/2000 | Colvin et al. | |
| 6,068,603 A | 5/2000 | Suzuki | |
| 6,068,629 A | 5/2000 | Haissaguerre et al. | |
| 6,071,233 A | 6/2000 | Ishikawa et al. | |
| 6,074,408 A | 6/2000 | Freeman | |
| 6,086,530 A | 7/2000 | Mack | |
| 6,090,108 A | 7/2000 | McBrayer et al. | |
| 6,096,046 A | 8/2000 | Weiss | |
| 6,102,926 A | 8/2000 | Tartaglia et al. | |
| 6,110,154 A | 8/2000 | Shimomura et al. | |
| 6,110,183 A | 8/2000 | Cope | |
| 6,113,593 A | 9/2000 | Tu et al. | |
| 6,117,144 A | 9/2000 | Nobles et al. | |
| 6,117,158 A | 9/2000 | Measamer et al. | |
| 6,139,555 A | 10/2000 | Hart et al. | |
| 6,146,391 A | 11/2000 | Cigaina | |
| 6,148,222 A | 11/2000 | Ramsey, III | |
| 6,149,653 A | 11/2000 | Deslauriers | |
| 6,149,662 A | 11/2000 | Pugliesi et al. | |
| 6,159,200 A | 12/2000 | Verdura et al. | |
| 6,165,184 A | 12/2000 | Verdura et al. | |
| 6,168,570 B1 | 1/2001 | Ferrera | |
| 6,168,605 B1 | 1/2001 | Measamer et al. | |
| 6,170,130 B1 | 1/2001 | Hamilton et al. | |
| 6,179,776 B1 | 1/2001 | Adams et al. | |
| 6,179,837 B1 | 1/2001 | Hooven | |
| 6,183,420 B1 | 2/2001 | Douk et al. | |
| 6,190,353 B1 | 2/2001 | Makower et al. | |
| 6,190,384 B1 | 2/2001 | Ouchi | |
| 6,190,399 B1 | 2/2001 | Palmer et al. | |
| 6,203,533 B1 | 3/2001 | Ouchi | |
| 6,206,872 B1 | 3/2001 | Lafond et al. | |
| 6,206,877 B1 | 3/2001 | Kese et al. | |
| 6,214,007 B1 | 4/2001 | Anderson | |
| 6,228,096 B1* | 5/2001 | Marchand | 606/139 |
| 6,245,079 B1 | 6/2001 | Nobles et al. | |
| 6,246,914 B1 | 6/2001 | de la Rama et al. | |
| 6,258,064 B1 | 7/2001 | Smith et al. | |
| 6,261,242 B1 | 7/2001 | Roberts et al. | |
| 6,264,664 B1 | 7/2001 | Avellanet | |
| 6,270,497 B1 | 8/2001 | Sekino et al. | |
| 6,270,505 B1 | 8/2001 | Yoshida et al. | |
| 6,277,136 B1 | 8/2001 | Bonutti | |
| 6,283,963 B1 | 9/2001 | Regula | |
| 6,293,909 B1 | 9/2001 | Chu et al. | |
| 6,293,952 B1 | 9/2001 | Brosens et al. | |
| 6,296,630 B1 | 10/2001 | Altman et al. | |
| 6,322,578 B1 | 11/2001 | Houle et al. | |
| 6,326,177 B1 | 12/2001 | Schoenbach et al. | |
| 6,328,730 B1 | 12/2001 | Harkrider, Jr. | |
| 6,350,267 B1 | 2/2002 | Stefanchik | |
| 6,350,278 B1 | 2/2002 | Lenker et al. | |
| 6,352,503 B1 | 3/2002 | Matsui et al. | |
| 6,352,543 B1 | 3/2002 | Cole | |
| 6,355,035 B1 | 3/2002 | Manushakian | |
| 6,371,956 B1 | 4/2002 | Wilson et al. | |
| 6,379,366 B1 | 4/2002 | Fleischman et al. | |
| 6,383,195 B1 | 5/2002 | Richard | |
| 6,383,197 B1 | 5/2002 | Conlon et al. | |
| 6,391,029 B1 | 5/2002 | Hooven et al. | |
| 6,402,735 B1 | 6/2002 | Langevin | |
| 6,406,440 B1 | 6/2002 | Stefanchik | |
| 6,409,733 B1 | 6/2002 | Conlon et al. | |
| 6,431,500 B1 | 8/2002 | Jacobs et al. | |
| 6,447,511 B1 | 9/2002 | Slater | |
| 6,447,523 B1 | 9/2002 | Middleman et al. | |
| 6,454,783 B1 | 9/2002 | Piskun | |
| 6,454,785 B2 | 9/2002 | De Hoyos Garza | |
| 6,464,701 B1 | 10/2002 | Hooven et al. | |
| 6,475,104 B1 | 11/2002 | Lutz et al. | |
| 6,485,411 B1 | 11/2002 | Konstorum et al. | |
| 6,489,745 B1 | 12/2002 | Koreis | |
| 6,491,626 B1 | 12/2002 | Stone et al. | |
| 6,491,691 B1 | 12/2002 | Morley et al. | |
| 6,493,590 B1 | 12/2002 | Wessman et al. | |
| 6,494,893 B2 | 12/2002 | Dubrul et al. | |
| 6,503,192 B1 | 1/2003 | Ouchi | |
| 6,506,190 B1 | 1/2003 | Walshe | |
| 6,508,827 B1 | 1/2003 | Manhes | |
| 6,543,456 B1 | 4/2003 | Freeman | |
| 6,551,270 B1 | 4/2003 | Bimbo et al. | |
| 6,554,829 B2 | 4/2003 | Schulze et al. | |
| 6,558,384 B2 | 5/2003 | Mayenberger | |
| 6,562,035 B1 | 5/2003 | Levin | |
| 6,562,052 B2 | 5/2003 | Nobles et al. | |
| 6,569,159 B1 | 5/2003 | Edwards et al. | |
| 6,572,629 B2 | 6/2003 | Kalloo et al. | |
| 6,572,635 B1 | 6/2003 | Bonutti | |
| 6,575,988 B2 | 6/2003 | Rousseau | |
| 6,579,311 B1 | 6/2003 | Makower | |
| 6,585,642 B2 | 7/2003 | Christopher | |
| 6,585,717 B1 | 7/2003 | Wittenberger et al. | |
| 6,592,559 B1 | 7/2003 | Pakter et al. | |
| 6,592,603 B2 | 7/2003 | Lasner | |
| 6,602,262 B2 | 8/2003 | Griego et al. | |
| 6,605,105 B1 | 8/2003 | Cuschieri et al. | |
| 6,610,072 B1 | 8/2003 | Christy et al. | |
| 6,610,074 B2 | 8/2003 | Santilli | |
| 6,620,193 B1 | 9/2003 | Lau et al. | |
| 6,626,919 B1 | 9/2003 | Swanstrom | |
| 6,632,229 B1 | 10/2003 | Yamanouchi | |
| 6,638,286 B1 | 10/2003 | Burbank et al. | |
| 6,652,521 B2 | 11/2003 | Schulze | |
| 6,652,551 B1 | 11/2003 | Heiss | |
| 6,656,194 B1 | 12/2003 | Gannoe et al. | |
| 6,663,641 B1 | 12/2003 | Kovac et al. | |
| 6,666,854 B1 | 12/2003 | Lange | |
| 6,672,338 B1 | 1/2004 | Esashi et al. | |
| 6,673,058 B2 | 1/2004 | Snow | |
| 6,673,087 B1 | 1/2004 | Chang et al. | |
| 6,685,628 B2 | 2/2004 | Vu | |
| 6,685,724 B1 | 2/2004 | Haluck | |
| 6,692,445 B2 | 2/2004 | Roberts et al. | |
| 6,692,462 B2 | 2/2004 | Mackenzie et al. | |
| 6,699,180 B2 | 3/2004 | Kobayashi | |
| 6,699,256 B2 | 3/2004 | Logan et al. | |
| 6,699,263 B2 | 3/2004 | Cope | |
| 6,706,018 B2 | 3/2004 | Westlund et al. | |
| 6,708,066 B2 | 3/2004 | Herbst et al. | |
| 6,716,226 B2 | 4/2004 | Sixto, Jr. et al. | |
| 6,736,822 B2 | 5/2004 | McClellan et al. | |
| 6,740,030 B2 | 5/2004 | Martone et al. | |
| 6,743,240 B2 | 6/2004 | Smith et al. | |
| 6,749,560 B1 | 6/2004 | Konstorum et al. | |
| 6,749,609 B1 | 6/2004 | Lunsford et al. | |
| 6,752,768 B2 | 6/2004 | Burdorff et al. | |
| 6,752,811 B2 | 6/2004 | Chu et al. | |
| 6,752,822 B2 | 6/2004 | Jespersen | |
| 6,761,685 B2 | 7/2004 | Adams et al. | |
| 6,761,718 B2 | 7/2004 | Madsen | |
| 6,773,434 B2 | 8/2004 | Ciarrocca | |
| 6,780,151 B2 | 8/2004 | Grabover et al. | |
| 6,780,352 B2 | 8/2004 | Jacobson | |
| 6,783,491 B2 | 8/2004 | Saadat et al. | |
| 6,786,864 B2 | 9/2004 | Matsuura et al. | |
| 6,790,173 B2 | 9/2004 | Saadat et al. | |
| 6,795,728 B2 | 9/2004 | Chornenky et al. | |
| 6,800,056 B2 | 10/2004 | Tartaglia et al. | |
| 6,808,491 B2 | 10/2004 | Kortenbach et al. | |
| 6,824,548 B2 | 11/2004 | Smith et al. | |
| 6,837,847 B2 | 1/2005 | Ewers et al. | |
| 6,843,794 B2 | 1/2005 | Sixto, Jr. et al. | |

| Patent | Kind | Date | Inventor |
|---|---|---|---|
| 6,861,250 | B1 | 3/2005 | Cole et al. |
| 6,866,627 | B2 | 3/2005 | Nozue |
| 6,878,106 | B1 | 4/2005 | Herrmann |
| 6,878,110 | B2 | 4/2005 | Yang et al. |
| 6,884,213 | B2 | 4/2005 | Raz et al. |
| 6,887,255 | B2 | 5/2005 | Shimm |
| 6,896,683 | B1 | 5/2005 | Gadberry et al. |
| 6,908,427 | B2 | 6/2005 | Fleener et al. |
| 6,908,476 | B2 | 6/2005 | Jud et al. |
| 6,916,284 | B2 | 7/2005 | Moriyama |
| 6,918,871 | B2 | 7/2005 | Schulze |
| 6,926,725 | B2 | 8/2005 | Cooke et al. |
| 6,932,810 | B2 | 8/2005 | Ryan |
| 6,932,824 | B1 | 8/2005 | Roop et al. |
| 6,932,827 | B2 | 8/2005 | Cole |
| 6,939,327 | B2 | 9/2005 | Hall et al. |
| 6,942,613 | B2 | 9/2005 | Ewers et al. |
| 6,945,472 | B2 | 9/2005 | Wuttke et al. |
| 6,945,979 | B2 | 9/2005 | Kortenbach et al. |
| 6,958,035 | B2 | 10/2005 | Friedman et al. |
| 6,960,162 | B2 | 11/2005 | Saadat et al. |
| 6,960,163 | B2 | 11/2005 | Ewers et al. |
| 6,962,587 | B2 | 11/2005 | Johnson et al. |
| 6,964,662 | B2 | 11/2005 | Kidooka |
| 6,966,909 | B2 | 11/2005 | Marshall et al. |
| 6,966,919 | B2 | 11/2005 | Sixto, Jr. et al. |
| 6,967,462 | B1 | 11/2005 | Landis |
| 6,971,988 | B2 | 12/2005 | Orban, III |
| 6,972,017 | B2 | 12/2005 | Smith et al. |
| 6,974,411 | B2 | 12/2005 | Belson |
| 6,976,992 | B2 | 12/2005 | Sachatello et al. |
| 6,984,203 | B2 | 1/2006 | Tartaglia et al. |
| 6,984,205 | B2 | 1/2006 | Gazdzinski |
| 6,986,774 | B2 | 1/2006 | Middleman et al. |
| 6,988,987 | B2 | 1/2006 | Ishikawa et al. |
| 6,989,028 | B2 | 1/2006 | Lashinski et al. |
| 6,991,627 | B2 | 1/2006 | Madhani et al. |
| 6,994,708 | B2 | 2/2006 | Manzo |
| 6,997,931 | B2 | 2/2006 | Sauer et al. |
| 7,000,818 | B2 | 2/2006 | Shelton, IV et al. |
| 7,008,375 | B2 | 3/2006 | Weisel |
| 7,009,634 | B2 | 3/2006 | Iddan et al. |
| 7,010,340 | B2 | 3/2006 | Scarantino et al. |
| 7,020,531 | B1 | 3/2006 | Colliou et al. |
| 7,025,580 | B2 | 4/2006 | Heagy et al. |
| 7,029,435 | B2 | 4/2006 | Nakao |
| 7,029,438 | B2 | 4/2006 | Morin et al. |
| 7,035,680 | B2 | 4/2006 | Partridge et al. |
| 7,037,290 | B2 | 5/2006 | Gardeski et al. |
| 7,041,052 | B2 | 5/2006 | Saadat et al. |
| 7,052,489 | B2 | 5/2006 | Griego et al. |
| 7,060,024 | B2 | 6/2006 | Long et al. |
| 7,060,025 | B2 | 6/2006 | Long et al. |
| 7,063,697 | B2 | 6/2006 | Slater |
| 7,063,715 | B2 | 6/2006 | Onuki et al. |
| 7,066,879 | B2 | 6/2006 | Fowler et al. |
| 7,066,936 | B2 | 6/2006 | Ryan |
| 7,070,602 | B2 | 7/2006 | Smith et al. |
| 7,076,305 | B2 | 7/2006 | Imran et al. |
| 7,083,629 | B2 | 8/2006 | Weller et al. |
| 7,087,071 | B2 | 8/2006 | Nicholas et al. |
| 7,090,673 | B2 | 8/2006 | Dycus et al. |
| 7,090,685 | B2 | 8/2006 | Kortenbach et al. |
| 7,093,518 | B2 | 8/2006 | Gmeilbauer |
| 7,101,371 | B2 | 9/2006 | Dycus et al. |
| 7,101,372 | B2 | 9/2006 | Dycus et al. |
| 7,101,373 | B2 | 9/2006 | Dycus et al. |
| 7,105,000 | B2 | 9/2006 | McBrayer |
| 7,105,005 | B2 | 9/2006 | Blake |
| 7,108,703 | B2 | 9/2006 | Danitz et al. |
| 7,112,208 | B2 | 9/2006 | Morris et al. |
| 7,115,092 | B2 | 10/2006 | Park et al. |
| 7,118,531 | B2 | 10/2006 | Krill |
| 7,118,578 | B2 * | 10/2006 | West et al. .................. 606/88 |
| 7,118,587 | B2 | 10/2006 | Dycus et al. |
| 7,128,708 | B2 | 10/2006 | Saadat et al. |
| RE39,415 | E | 11/2006 | Bales et al. |
| 7,131,978 | B2 | 11/2006 | Sancoff et al. |
| 7,131,979 | B2 | 11/2006 | DiCarlo et al. |
| 7,131,980 | B1 | 11/2006 | Field et al. |
| 7,137,980 | B2 | 11/2006 | Buysse et al. |
| 7,137,981 | B2 | 11/2006 | Long |
| 7,146,984 | B2 | 12/2006 | Stack et al. |
| 7,147,650 | B2 | 12/2006 | Lee |
| 7,153,321 | B2 | 12/2006 | Andrews |
| 7,163,525 | B2 | 1/2007 | Franer |
| 7,172,714 | B2 | 2/2007 | Jacobson |
| 7,179,254 | B2 | 2/2007 | Pendekanti et al. |
| 7,195,612 | B2 | 3/2007 | Van Sloten et al. |
| 7,195,631 | B2 | 3/2007 | Dumbauld |
| 7,208,005 | B2 | 4/2007 | Frecker et al. |
| 7,211,092 | B2 | 5/2007 | Hughett |
| 7,223,272 | B2 | 5/2007 | Francese et al. |
| 7,232,414 | B2 | 6/2007 | Gonzalez |
| 7,232,445 | B2 | 6/2007 | Kortenbach et al. |
| 7,241,290 | B2 | 7/2007 | Doyle et al. |
| 7,244,228 | B2 | 7/2007 | Lubowski |
| 7,252,660 | B2 | 8/2007 | Kunz |
| 7,270,663 | B2 | 9/2007 | Nakao |
| 7,294,139 | B1 | 11/2007 | Gengler |
| 7,301,250 | B2 | 11/2007 | Cassel |
| 7,306,597 | B2 | 12/2007 | Manzo |
| 7,318,802 | B2 | 1/2008 | Suzuki et al. |
| 7,320,695 | B2 | 1/2008 | Carroll |
| 7,322,934 | B2 | 1/2008 | Miyake et al. |
| 7,323,006 | B2 | 1/2008 | Andreas et al. |
| 7,329,257 | B2 | 2/2008 | Kanehira et al. |
| 7,329,383 | B2 | 2/2008 | Stinson |
| 7,344,536 | B1 | 3/2008 | Lunsford et al. |
| 7,352,387 | B2 | 4/2008 | Yamamoto |
| 7,364,582 | B2 | 4/2008 | Lee |
| 7,371,215 | B2 | 5/2008 | Colliou et al. |
| 7,381,216 | B2 | 6/2008 | Buzzard et al. |
| 7,393,322 | B2 | 7/2008 | Wenchell |
| 7,402,162 | B2 | 7/2008 | Ouchi |
| 7,404,791 | B2 | 7/2008 | Linares et al. |
| 7,413,563 | B2 | 8/2008 | Corcoran et al. |
| 7,416,554 | B2 | 8/2008 | Lam et al. |
| 7,422,590 | B2 | 9/2008 | Kupferschmid et al. |
| 7,435,257 | B2 | 10/2008 | Lashinski et al. |
| 7,452,327 | B2 | 11/2008 | Durgin et al. |
| 7,455,208 | B2 | 11/2008 | Wales et al. |
| 7,468,066 | B2 | 12/2008 | Vargas et al. |
| 7,488,295 | B2 | 2/2009 | Burbank et al. |
| 7,497,867 | B2 | 3/2009 | Lasner et al. |
| 7,507,200 | B2 | 3/2009 | Okada |
| 7,524,281 | B2 | 4/2009 | Chu et al. |
| 7,524,302 | B2 | 4/2009 | Tower |
| 7,534,228 | B2 | 5/2009 | Williams |
| 7,544,203 | B2 | 6/2009 | Chin et al. |
| 7,548,040 | B2 | 6/2009 | Lee et al. |
| 7,549,564 | B2 | 6/2009 | Boudreaux |
| 7,553,278 | B2 | 6/2009 | Kucklick |
| 7,553,298 | B2 | 6/2009 | Hunt et al. |
| 7,559,887 | B2 | 7/2009 | Dannan |
| 7,560,006 | B2 | 7/2009 | Rakos et al. |
| 7,561,916 | B2 | 7/2009 | Hunt et al. |
| 7,566,334 | B2 | 7/2009 | Christian et al. |
| 7,575,144 | B2 | 8/2009 | Ortiz et al. |
| 7,579,550 | B2 | 8/2009 | Dayton et al. |
| 7,582,096 | B2 | 9/2009 | Gellman et al. |
| 7,588,177 | B2 | 9/2009 | Racenet |
| 7,588,557 | B2 | 9/2009 | Nakao |
| 7,618,398 | B2 | 11/2009 | Holman et al. |
| 7,632,250 | B2 | 12/2009 | Smith et al. |
| 7,635,373 | B2 | 12/2009 | Ortiz |
| 7,637,903 | B2 | 12/2009 | Lentz et al. |
| 7,651,483 | B2 | 1/2010 | Byrum et al. |
| 7,651,509 | B2 | 1/2010 | Bojarski et al. |
| 7,654,431 | B2 | 2/2010 | Hueil et al. |
| 7,662,089 | B2 | 2/2010 | Okada et al. |
| 7,666,180 | B2 | 2/2010 | Holsten et al. |
| 7,713,270 | B2 | 5/2010 | Suzuki |
| 7,736,374 | B2 | 6/2010 | Vaughan et al. |
| 7,762,998 | B2 | 7/2010 | Birk et al. |
| 7,771,416 | B2 | 8/2010 | Spivey et al. |
| 7,780,683 | B2 | 8/2010 | Roue et al. |
| 7,794,475 | B2 | 9/2010 | Hess et al. |

| Patent/Publication No. | Date | Inventor(s) |
|---|---|---|
| 7,837,615 B2 | 11/2010 | Le et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,896,887 B2 | 3/2011 | Rimbaugh et al. |
| 7,918,869 B2 | 4/2011 | Saadat et al. |
| 7,931,624 B2 | 4/2011 | Smith et al. |
| 7,947,000 B2 | 5/2011 | Vargas et al. |
| 7,955,298 B2 | 6/2011 | Carroll et al. |
| 7,963,975 B2 | 6/2011 | Criscuolo |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114732 A1 | 6/2003 | Webler et al. |
| 2003/0120257 A1 | 6/2003 | Houston et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0002735 A1 | 1/2004 | Lizardi et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |

| | | | | | | |
|---|---|---|---|---|---|---|
| 2006/0025812 A1 | 2/2006 | Shelton, IV | | 2007/0043345 A1 | 2/2007 | Davalos et al. |
| 2006/0025819 A1 | 2/2006 | Nobis et al. | | 2007/0049800 A1 | 3/2007 | Boulais |
| 2006/0036267 A1 | 2/2006 | Saadat et al. | | 2007/0049902 A1 | 3/2007 | Griffin et al. |
| 2006/0041188 A1 | 2/2006 | Dirusso et al. | | 2007/0051375 A1 | 3/2007 | Milliman |
| 2006/0058582 A1 | 3/2006 | Maahs et al. | | 2007/0060880 A1 | 3/2007 | Gregorich et al. |
| 2006/0058776 A1 | 3/2006 | Bilsbury | | 2007/0067017 A1 | 3/2007 | Trapp |
| 2006/0069396 A1 | 3/2006 | Meade et al. | | 2007/0073102 A1 | 3/2007 | Matsuno et al. |
| 2006/0069424 A1 | 3/2006 | Acosta et al. | | 2007/0073269 A1 | 3/2007 | Becker |
| 2006/0074413 A1 | 4/2006 | Behzadian | | 2007/0079924 A1 | 4/2007 | Saadat et al. |
| 2006/0079890 A1 | 4/2006 | Guerra | | 2007/0088370 A1 | 4/2007 | Kahle et al. |
| 2006/0089528 A1 | 4/2006 | Tartaglia et al. | | 2007/0100375 A1 | 5/2007 | Mikkaichi et al. |
| 2006/0095060 A1 | 5/2006 | Mayenberger et al. | | 2007/0100376 A1 | 5/2007 | Mikkaichi et al. |
| 2006/0100687 A1 | 5/2006 | Fahey et al. | | 2007/0106118 A1 | 5/2007 | Moriyama |
| 2006/0106423 A1 | 5/2006 | Weisel et al. | | 2007/0112251 A1 | 5/2007 | Nakhuda |
| 2006/0111209 A1 | 5/2006 | Hinman et al. | | 2007/0112331 A1 | 5/2007 | Weber et al. |
| 2006/0111210 A1 | 5/2006 | Hinman et al. | | 2007/0112342 A1 | 5/2007 | Pearson et al. |
| 2006/0111704 A1 | 5/2006 | Brenneman et al. | | 2007/0112383 A1 | 5/2007 | Conlon et al. |
| 2006/0129166 A1 | 6/2006 | Lavelle | | 2007/0112384 A1 | 5/2007 | Conlon et al. |
| 2006/0135962 A1 | 6/2006 | Kick et al. | | 2007/0112385 A1 | 5/2007 | Conlon |
| 2006/0135971 A1 | 6/2006 | Swanstrom et al. | | 2007/0112417 A1 | 5/2007 | Shanley et al. |
| 2006/0135984 A1 | 6/2006 | Kramer et al. | | 2007/0112425 A1 | 5/2007 | Schaller et al. |
| 2006/0142644 A1 | 6/2006 | Mulac et al. | | 2007/0118115 A1 | 5/2007 | Artale et al. |
| 2006/0142652 A1 | 6/2006 | Keenan | | 2007/0123840 A1 | 5/2007 | Cox |
| 2006/0142790 A1 | 6/2006 | Gertner | | 2007/0129605 A1 | 6/2007 | Schaaf |
| 2006/0142798 A1 | 6/2006 | Holman et al. | | 2007/0129719 A1 | 6/2007 | Kendale et al. |
| 2006/0149132 A1 | 7/2006 | Iddan | | 2007/0129760 A1 | 6/2007 | Demarais et al. |
| 2006/0149135 A1 | 7/2006 | Paz | | 2007/0135709 A1 | 6/2007 | Rioux et al. |
| 2006/0161190 A1 | 7/2006 | Gadberry et al. | | 2007/0142706 A1 | 6/2007 | Matsui et al. |
| 2006/0167416 A1 | 7/2006 | Mathis et al. | | 2007/0156127 A1 | 7/2007 | Rioux et al. |
| 2006/0167482 A1 | 7/2006 | Swain et al. | | 2007/0161855 A1 | 7/2007 | Mikkaichi et al. |
| 2006/0178560 A1 | 8/2006 | Saadat et al. | | 2007/0173691 A1 | 7/2007 | Yokoi et al. |
| 2006/0183975 A1 | 8/2006 | Saadat et al. | | 2007/0173869 A1 | 7/2007 | Gannoe et al. |
| 2006/0184161 A1 | 8/2006 | Maahs et al. | | 2007/0173870 A2 | 7/2007 | Zacharias |
| 2006/0189844 A1 | 8/2006 | Tien | | 2007/0173872 A1 | 7/2007 | Neuenfeldt |
| 2006/0189845 A1 | 8/2006 | Maahs et al. | | 2007/0179525 A1 | 8/2007 | Frecker et al. |
| 2006/0190027 A1 | 8/2006 | Downey | | 2007/0179530 A1 | 8/2007 | Tieu et al. |
| 2006/0195084 A1 | 8/2006 | Slater | | 2007/0197865 A1 | 8/2007 | Miyake et al. |
| 2006/0200005 A1 | 9/2006 | Bjork et al. | | 2007/0198057 A1 | 8/2007 | Gelbart et al. |
| 2006/0200169 A1 | 9/2006 | Sniffin | | 2007/0203487 A1 | 8/2007 | Sugita |
| 2006/0200170 A1 | 9/2006 | Aranyi | | 2007/0208364 A1 | 9/2007 | Smith et al. |
| 2006/0200199 A1 | 9/2006 | Bonutti et al. | | 2007/0213754 A1 | 9/2007 | Mikkaichi et al. |
| 2006/0217665 A1 | 9/2006 | Prosek | | 2007/0225554 A1 | 9/2007 | Maseda et al. |
| 2006/0217697 A1 | 9/2006 | Lau et al. | | 2007/0233040 A1 | 10/2007 | Macnamara et al. |
| 2006/0217742 A1 | 9/2006 | Messerly et al. | | 2007/0244358 A1 | 10/2007 | Lee |
| 2006/0217743 A1 | 9/2006 | Messerly et al. | | 2007/0250038 A1 | 10/2007 | Boulais |
| 2006/0229639 A1 | 10/2006 | Whitfield | | 2007/0250057 A1 | 10/2007 | Nobis et al. |
| 2006/0229640 A1 | 10/2006 | Whitfield | | 2007/0255096 A1 | 11/2007 | Stefanchik et al. |
| 2006/0237022 A1 | 10/2006 | Chen et al. | | 2007/0255100 A1 | 11/2007 | Barlow et al. |
| 2006/0237023 A1 | 10/2006 | Cox et al. | | 2007/0255273 A1 | 11/2007 | Fernandez et al. |
| 2006/0241570 A1 | 10/2006 | Wilk | | 2007/0255303 A1 | 11/2007 | Bakos et al. |
| 2006/0247576 A1 | 11/2006 | Poncet | | 2007/0255306 A1 | 11/2007 | Conlon et al. |
| 2006/0247673 A1 | 11/2006 | Voegele et al. | | 2007/0260112 A1 | 11/2007 | Rahmani |
| 2006/0253004 A1 | 11/2006 | Frisch et al. | | 2007/0260117 A1 | 11/2007 | Zwolinski et al. |
| 2006/0253039 A1 | 11/2006 | McKenna et al. | | 2007/0260121 A1 | 11/2007 | Bakos et al. |
| 2006/0258907 A1 | 11/2006 | Stefanchik et al. | | 2007/0260273 A1 | 11/2007 | Cropper et al. |
| 2006/0258908 A1 | 11/2006 | Stefanchik et al. | | 2007/0270629 A1 | 11/2007 | Charles |
| 2006/0258910 A1 | 11/2006 | Stefanchik et al. | | 2007/0270889 A1 | 11/2007 | Conlon et al. |
| 2006/0258954 A1 | 11/2006 | Timberlake et al. | | 2007/0270895 A1 | 11/2007 | Nobis et al. |
| 2006/0258955 A1 | 11/2006 | Hoffman et al. | | 2007/0270907 A1 | 11/2007 | Stokes et al. |
| 2006/0259010 A1 | 11/2006 | Stefanchik et al. | | 2007/0282371 A1 | 12/2007 | Lee et al. |
| 2006/0264752 A1 | 11/2006 | Rubinsky et al. | | 2007/0299387 A1 | 12/2007 | Williams et al. |
| 2006/0264904 A1 | 11/2006 | Kerby et al. | | 2008/0004650 A1 | 1/2008 | George |
| 2006/0264930 A1 | 11/2006 | Nishimura | | 2008/0015409 A1 | 1/2008 | Barlow et al. |
| 2006/0270902 A1 | 11/2006 | Igarashi et al. | | 2008/0015552 A1 | 1/2008 | Doyle et al. |
| 2006/0271102 A1 | 11/2006 | Bosshard et al. | | 2008/0027387 A1 | 1/2008 | Grabinsky |
| 2006/0276835 A1 | 12/2006 | Uchida | | 2008/0033451 A1 | 2/2008 | Rieber et al. |
| 2006/0281970 A1 | 12/2006 | Stokes et al. | | 2008/0051629 A1 | 2/2008 | Sugiyama et al. |
| 2006/0282106 A1 | 12/2006 | Cole et al. | | 2008/0051735 A1 | 2/2008 | Measamer et al. |
| 2006/0285732 A1 | 12/2006 | Horn et al. | | 2008/0058586 A1 | 3/2008 | Karpiel |
| 2006/0287644 A1 | 12/2006 | Inganas et al. | | 2008/0065169 A1 | 3/2008 | Colliou et al. |
| 2006/0287666 A1 | 12/2006 | Saadat et al. | | 2008/0071264 A1 | 3/2008 | Azure |
| 2006/0293626 A1 | 12/2006 | Byrum et al. | | 2008/0086172 A1 | 4/2008 | Martin et al. |
| 2007/0002135 A1 | 1/2007 | Glukhovsky | | 2008/0097472 A1 | 4/2008 | Agmon et al. |
| 2007/0005019 A1 | 1/2007 | Okishige | | 2008/0097483 A1 | 4/2008 | Ortiz et al. |
| 2007/0015965 A1 | 1/2007 | Cox et al. | | 2008/0103527 A1 | 5/2008 | Martin et al. |
| 2007/0016225 A1 | 1/2007 | Nakao | | 2008/0114384 A1 | 5/2008 | Chang et al. |
| 2007/0032700 A1 | 2/2007 | Fowler et al. | | 2008/0119870 A1 | 5/2008 | Williams |
| 2007/0032701 A1 | 2/2007 | Fowler et al. | | 2008/0125796 A1 | 5/2008 | Graham |
| 2007/0043261 A1 | 2/2007 | Watanabe et al. | | 2008/0132892 A1 | 6/2008 | Lunsford et al. |

| | | |
|---|---|---|
| 2008/0139882 A1 | 6/2008 | Fujimori |
| 2008/0147113 A1 | 6/2008 | Nobis et al. |
| 2008/0171907 A1 | 7/2008 | Long et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200912 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0082776 A1* | 3/2009 | Cresina .................. 606/103 |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0198231 A1 | 8/2009 | Esser et al. |
| 2009/0227828 A1 | 9/2009 | Swain et al. |
| 2009/0248055 A1 | 10/2009 | Spivey et al. |
| 2009/0281559 A1 | 11/2009 | Swain et al. |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0249700 A1 | 9/2010 | Spivey |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331774 A2 | 12/2010 | Spivey |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |

FOREIGN PATENT DOCUMENTS

| | | |
|---|---|---|
| DE | 3008120 A1 | 9/1980 |
| DE | 4323585 A1 | 1/1995 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |

| | | |
|---|---|---|
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 1769749 B1 | 11/2009 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 8-29699 A | 2/1996 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 01/10319 A1 | 2/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/101075 A2 | 8/2008 |
| WO | WO 2008/102154 A2 | 8/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/080974 A1 | 7/2010 |
| WO | WO 2010/088481 A1 | 8/2010 |

OTHER PUBLICATIONS

U.S. Appl. No. 11/744,279, filed May 4, 2007.
U.S. Appl. No. 11/796,035, filed Apr. 26, 2007.
Michael S. Kavic, M.D., "Natural Orifice Translumenal Endoscopic Surgery: "NOTES"", JSLS, vol. 10, pp. 133-134 (2006).
Guido M. Sclabas, M.D., et al., "Endoluminal Methods for Gastrotomy Closure in Natural Orifice TransEnteric Surgery (Notes)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.

M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vasc Intery Radiol, (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.

C. Cope et al., "Long Term Patency of Experimental Magnetic Compression Gastroenteric Anastomoses Achieved with Covered Stents," Gastrointest Endosc, (2001), vol. 53, pp. 780-784.

H. Okajima et al., "Magnet Compression Anastamosis for Bile Duct Stenosis After Duct to Duct Biliary Reconstruction in Living Donor Liver Transplantation," Liver Transplantation (2005), pp. 473-475.

A. Fritscher-Ravens et al., "Transluminal Endosurgery: Single Lumen Access Anastamotic Device for Flexible Endoscopy," Gastrointestinal Endosc, (2003), vol. 58(4), pp. 585-591.

G.A. Hallenbeck, M.D. et al., "An Instrument for Colorectal Anastomosis Without Sutrues," Dis Col Rectum, (1963), vol. 5, pp. 98-101.

T. Hardy, Jr., M.D. et al., "A Biofragmentable Ring for Sutureless Bowel Anastomosis. An Experimental Study," Dis col. Rectum, (1985), vol. 28, pp. 484-490.

P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL: http://www.usgimedical.com/eos/components-gprox.htm—accessed May 30, 2008 (2 pages).

Printout of web page—http://www.vacumed.com/zconn/product/Product.do?compid=27&prodid=852, #51XX Low-Cost Permanent Tubes 2MM ID, Smooth Interior Walls, VacuMed, Ventura, California, Accessed Jul. 24, 2007.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, August (2007), pp. 255-259.

U.S. Appl. No. 11/796,357, filed Apr. 27, 2007.
U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489 filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.

International Search Report and Written Opinion for PCT/US2009/045597, Aug. 6, 2009 (15 pages).

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview&navRelId=1000.1003&method=D..., accessed Jul. 18, 2008 (4 pages).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis," The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).

D. Wilhelm et al., "An Innovative, Safe and Sterile Sigmoid Access (ISSA) for NOTES," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and for DNA electrotransfer for gene therapy," Biochimica et Biophysica Acta, 1523, pp. 73-83 (2000).

Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation in Vivo," The Journal of Immunology, 164, pp. 4635-4640 (2000).

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented at DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).

Castellvi et al., "Hybrid Transvaginal NOTES Sleeve Gastrectomy in a Pocine Model Using a Magnetically Anchored Camera and Novel Instrumentation," Abstract submitted along with Poster at SAGES Annual Meeting in Phoenix, AZ, Apr. 22, 2009 (1 page).

Castellvi et al., "Hybrid Transvaginal NOTES Sleeve Gastrectomy in a Pocine Model Using a Magnetically Anchored Camera and Novel Instrumentation," Poster submitted along with Abstract at SAGES Annual Meeting in Phoenix, AZ, Apr. 22, 2009 (1 page).

U.S. Appl. No. 12/060,601, filed Apr. 1, 2008.
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.

Ethicon, Inc., "Wound Closure Manual: Chapter 3 (The Surgical Needle)," 15 pages, (1994).

OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).

Hakko Retractors, obtained Aug. 25, 2009 (5 pages).
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/752,701, filed Apr. 1, 2010.

Zadno et al., "Linear Superelasticity in Cold-Worked NI-TI," Engineering Aspects of Shape Memory Alloys, pp. 414-419 (1990).

U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.

* cited by examiner

ENDOSCOPIC SUTURING TENSION CONTROLLING AND INDICATION DEVICES

FIELD OF THE INVENTION

The present invention relates, in general, to surgical fasteners and devices for approximating and fastening tissue and, more particularly, to devices and methods relating to identifying and limiting the amount of tension experienced by an endoscopically applied suture.

BACKGROUND OF THE INVENTION

Endoscopic microsurgery, including procedures performed by way of endoscopic instruments such as gastroscopes, colonoscopes, laparoscopes, and the like, may be preferred as an alternative to open surgery due to the many advantages attributed to such "minimally invasive" techniques such as shortened hospital stays, reduced recovery time, reduced risk of complications, and diminishment of the amount of and/or visibility of scarring caused by a surgical intervention. In many endoscopic procedures, as in open surgery, there are instances where a surgeon may desire to repair damaged or diseased tissues by apposing the tissues together using a suture. However, the suturing devices, stapling devices, and other fastener applicators that have been developed to aid surgeons in performing open surgery generally cannot be easily redesigned to be passed through a flexible endoscopic instrument, which may have a working channel having an internal diameter in the range of about 2.5 to about 4.0 millimeters.

Some gastric restriction procedures utilize a series of fasteners that are coupled together by a suture used to cinch and pull the fastened tissue together. Suture coupled fasteners offer the advantage of allowing the fasteners to be applied to each wall of the stomach separately and then to be cinched together using the suture after the fastener applying device is removed. In order to apply staples, on the other hand, folds must be created in each wall to engage and pull the tissue together, thus requiring that the staples be inserted through four walls of tissue.

To address these problems, various suture anchors and applicator devices have been developed to permit surgeons to endoscopically emplace sutures within tissues. Such suture anchors may be deployed using applicator devices that are inserted within and extended through the working channel of an endoscope, carrying a suture anchor to the site of the repair. Such applicators typically include a cannulated needle portion which permits the surgeon to penetrate the tissues adjacent to diseased or damaged tissue and deploy the suture anchor within, or preferably onto a distal surface of, the tissue to be apposed in repair.

The suture anchor is generally attached to a distal end of a suture, with the bulk of the suture extending alongside or within a portion of the applicator device, and with a proximal end of the suture trailing outside the endoscopic instrument. After deploying the suture anchors, the surgeon may appose the tissue by applying tension to the proximal ends of the sutures, thereby manipulating the suture anchors and the surrounding tissues, and secure the apposed tissue by advancing a series of half hitches towards the repair site using a knot pusher device. Alternately, the surgeon may thread the trailing ends of the sutures through one of a number of types of knotting elements and associated knotting element applicators, feed the applicator through the flexible endoscope towards the apposed tissue, and "fire" the applicator to fix or "knot" the sutures in place with the knotting element. Examples of such suture locking and knotting devices are disclosed in U.S. Patent Application Publication No. US 2007/0270907 A1, to Michael J. Stokes et al., entitled "Suture Locking Device", filed May 19, 2006, and U.S. Patent Application Publication No. US 2007/0270889 to Sean P. Conlon et al., entitled "Combination Knotting Element and Suture Anchor Applicator", filed May 19, 2006, the disclosures of each said published applications being herein incorporated by reference in their respective entireties.

While suture-coupled fasteners may be more advantageous than staples in some applications, slack or loops of excess suture can form as the surgeon is attaching the fasteners to the opposed walls of the stomach. For a gastric restriction procedure to be successful, for example, the suture must be tightly cinched to pull the gastric walls together so that the reduced volume of the patient's stomach can be maintained. If any slack or loose loops of suture are present, the stomach will expand and the restriction will not be effective. Thus, the surgeon must maintain tension on the suture as the fasteners are being applied and the sutures are "knotted" or otherwise fastened together. Moreover, because of the relatively long distances traveled by endoscopic devices, user forces are not generally transmitted in a one-to-one fashion with respect to time and magnitude. As a result, tactile feedback to the surgeon is generally poor. This makes tension control of resulting stitches difficult. Too much tension can cause tissue necrosis, while insufficient tension can cause peritonitis or other issues associated with a loose stitch, such as malfunction of the suturing device. These problems are also encountered when suturing within the gastrointenstinal ("GI") tract wherein two pieces of sutures are locked together, during general tissue approximation.

Consequently a need exists for devices that can manage and/or indicate the amount of tension applied to a suture prior to the sutures being locked together.

The foregoing discussion is intended only to illustrate some of the shortcomings present in the field of the invention at the time, and should not be taken as a disavowal of claim scope.

SUMMARY

In one aspect of the invention, there is provided a suture tensioning device. Various embodiments of the device may comprise a housing and a movable tensioning member that is constrained to move axially within the housing. The movable tensioning member may be configured to have a portion of a suture wound therearound such that a distal portion of the suture extends in a distal direction from the movable tensioning member to be anchored to tissue. A proximal portion of the suture may protrude from the movable tensioning member to have tension applied thereto. Various embodiments may further include a first resilient member for applying a first resistive force to the movable tensioning member in a first direction and a second resilient member for applying a second resistive force to the movable tensioning member in a second direction that is opposite to the first direction.

In another general aspect of various embodiments of the present invention, there is provided a suture application device that may include a handle assembly and a cannula that is operably supported by the handle assembly and is configured to be operably coupled to an end effector for applying a suture to a surgical site. The device may further include a movable tensioning member that is constrained to move axially within a portion of the handle assembly. The movable tensioning member may be configured to have a portion of a suture wound therearound such that a distal portion of the suture extends in a distal direction from the movable tensioning member to be anchored to tissue and a proximal portion of the suture protrudes from the movable tensioning member to have tension applied thereto. The device may also include a first resilient member for applying a first resistive force to the movable tensioning member in a first direction and a second resilient member for applying a second resistive force to the movable tensioning member in a second direction that is opposite to the first direction.

In still another general aspect of various embodiments of the present invention, there is provided a suture locking device. Various embodiments may include a housing member and a first locking element that is operably supported within the housing member and has a suture extending therethrough. A second locking element may be supported relative to the first locking element and be configured to retainingly engage the first locking element upon application of a firing motion to the first locking element to thereby cause a portion of the suture extending through the first locking element to be locked between the first and second locking elements. An indicator member may be supported within the housing member and be configured to only be viewable through an external wall thereof when an excessive amount of tension has been applied to the suture material prior to applying the firing motion to the first locking member.

In accordance with another general aspect of the present invention there is provided a suture locking device. Various embodiments may include a handle member that is configured to generate a firing motion and an elongated catheter that extends from the handle member. A drive cable may extend through the elongated catheter and operably interface with the handle member for transmitting the firing motion to a first locking element that is operably coupled thereto. The first locking element may have a suture extending therethrough. A second locking element may be supported relative to said the first locking element and be configured to retainingly engage the first locking element upon application of a firing motion to the first locking element to thereby cause a portion of the suture extending through the first locking element to be locked between the first and second locking elements. An indicator member may be supported within the catheter and may be arranged to interface with the drive cable such that the indicator member is only be viewable through an external wall of the catheter when an excessive amount of tension has been applied to the suture material prior to applying the firing motion.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain various principles of the present invention.

DETAILED DESCRIPTION

Figure 1:
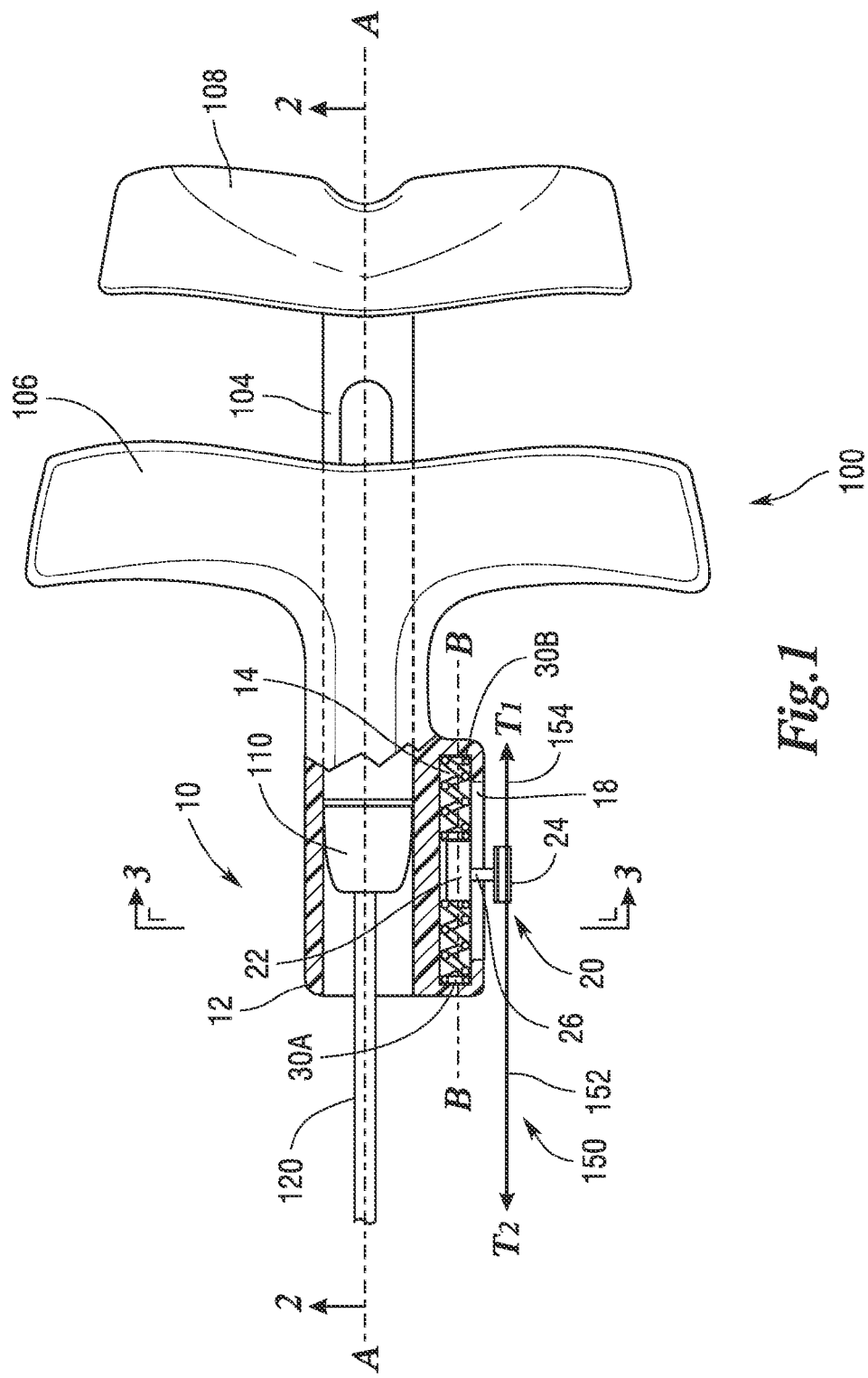
FIG. 1 is a side view of a handle assembly of a suturing device for delivering a suture to a surgical site that includes a suture tensioning device embodiment of the present invention, with portions thereof shown in cross-section for clarity.
Figure 2:
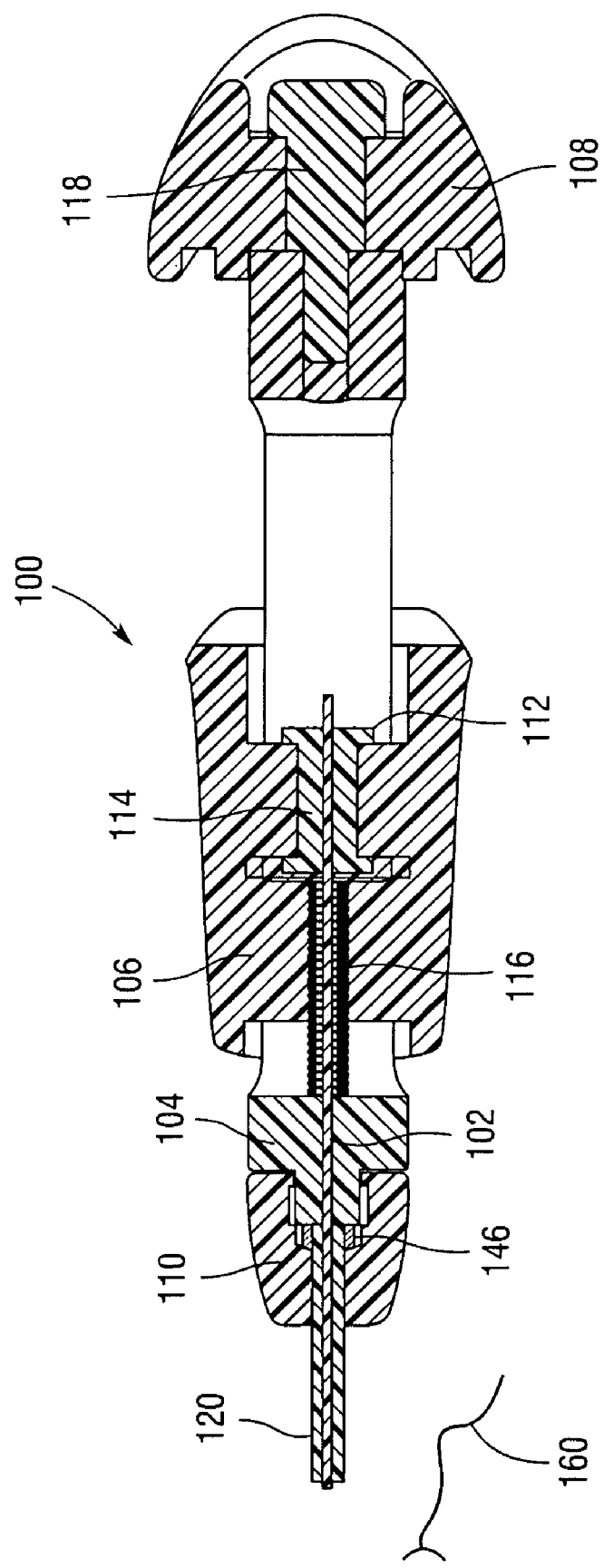
FIG. 2 is a cross-section of the handle assembly of FIG. 1 taken along line 2-2 in FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

It will be appreciated that the terms "proximal" and "distal" are used herein with reference to a clinician manipulating an end of the instrument that protrudes out of a patient's natural orifice, e.g., mouth, anus, vagina, etc. The term "proximal" referring to the portion closest to the clinician and the term "distal" referring to the portion located away from the clinician. It will be further appreciated that, for convenience and clarity, spatial terms such as "vertical", "horizontal", "up" and "down" may be used herein with respect to the drawings. However, surgical instruments are used in many orientations and positions, and these terms are not intended to be limiting and/or absolute.

The present invention generally relates to devices and methods that may be used in connection with controlling an amount of tension applied to a suture when employing a device used to knot or otherwise attach sutures together. FIGS. 1-5 illustrate one exemplary embodiment of a suture tensioning device 10 as used in connection with a suturing device for delivering a suture to a surgical site of the type described in Published U.S. Patent Application No. US 2007/0270907 A1, to Michael J. Stokes et al., entitled "Suture Locking Device", filed May 19, 2006, the disclosure of which has been herein incorporated by reference in its entirety. However, those of ordinary skill in the art will also readily appreciate that the features of various embodiments of the present invention may also be successfully employed, for example, in connection with those suturing devices disclosed in Published U.S. Patent Application No. US 2007/0270889 to Sean P. Conlon et al., entitled "Combination Knotting Element and Suture Anchor Applicator", filed May 19, 2006, the disclosure of which is herein incorporated by reference in its entirety, as well as other know suture locking devices.

In various embodiments, the suture tensioning device 10 may being incorporated into a handle 100 for deploying a knotting element from a suture locking device. Handle 100 may be attached at the proximal end of drive cable 102. Handle 100 may comprise a longitudinal body portion 104, as well as a grip portion 106 for engaging the surgeon's fingers during operation of the suture locking device. A thumb guide 108 may be located at the proximal end of handle 100. As shown in greater detail in FIG. 2, the distal end of handle 100 may include an outer clamp 110 that has a center bore for passage of catheter 120. A ring 146 may be welded to the proximal end of catheter 120 and retained between clamp 110 and handle body 104 to secure the catheter. Drive cable 102 may extend proximally beyond clamp 110 and catheter 120 into a center bore 112 of handle body 104. A retaining member 114 may be longitudinally disposed in bore 112 of handle body 104. Grip 106 may be attached to retaining member 114 to move the retaining member within handle body 104 in response to pressure applied to the grip by the surgeon.

Drive cable 102 is locked within retaining member 114 so as to move with the retaining member along the longitudinal axis "A-A" of handle body 104. A resilient member 116 extends about drive cable 102 between the proximal end of handle body 104 and retaining member 114. Resilient member 116 serves to bias a cable connector portion of the suture locking device into a proximal position within an adaptor thereof. An attachment mechanism 118 is lodged in the proximal end of handle body 104 to attach thumb guide 108 to the handle body 104, and to allow for rotation of the guide relative to the handle body 104. Tension is applied to drive cable 102 by pulling proximally on grip 106. As grip 106 moves proximally, retaining member 114 moves proximally within bore 112 of handle body 104, due to the connection between the grip and retaining member. As retaining member 114 moves proximally, the length of drive cable 102 is pulled proximally, increasing the tension on the cable 102. The increased tension on drive cable 102 is transferred to a launching member portion of the suture locking device. Handle body bore 112 is sized to allow drive cable 102 to be pulled a sufficient distance to so as to actuate the suture locking device as described in U.S. Patent Publication No. US2007/0270907, which has been herein incorporated by reference in its entirety.

As also described in that published application, the suture material 150 that has been externalized out of the patient's mouth (or other orifice or incision) is threaded into suture locking mechanism and thereafter, the ends of the suture 150 are retrieved by the surgeon. Following threading of suture material 150 into the suture locking device, the surgeon reintroduces the endoscope into the patient, and advances the scope to the suture site using the suture strands as a guide. In various procedures, it is desirable to maintain in-line tension on the suture material 150 while the suture locking device is passed towards the suture site by holding the externalized ends of the suture material. Once the suture locking device is in position at the suture site, tension is applied to suture material 150, as well as to handle 100, to fire the device as described in the aforementioned U.S. Published Patent Application US2007/0270907.

To facilitate the application of a desirable amount of tension to the suture material, the handle housing 100 may include a suture tensioning device 10 embodiment of the present invention. As can be seen in FIG. 1, the suture tensioning device 10 may include a housing 12 that has an axially extending passage 14 therein. The passage 14 may have an axis "B-B" that is substantially parallel to the handle axis "A-A" as shown. In the embodiment depicted in FIGS. 1-4, the housing 12 comprises an integral part of the grip 106. For example, the housing 12 and grip 106 may be integrally molded from a polymer material as a single piece or, in other embodiments, the housing 12 may be fabricated apart from the grip 106 and then attached thereto by, for example, an appropriate adhesive material or other suitable fastener arrangement.

Figure 3:
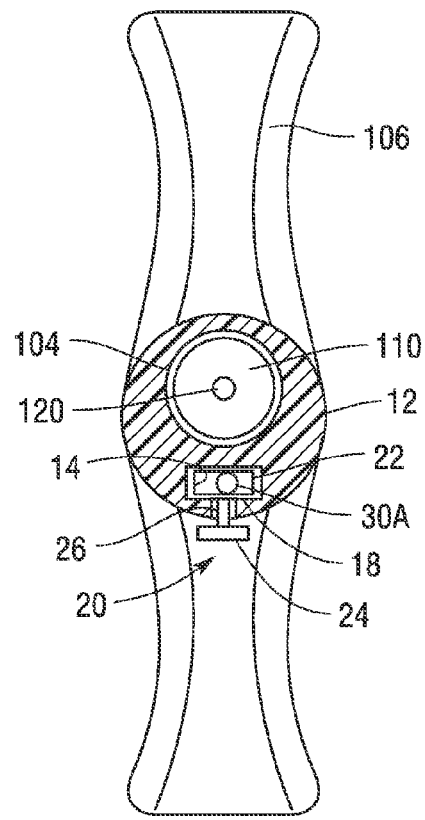
FIG. 3 is a cross-section of the handle assembly of FIG. 1 taken along line 3-3 in FIG. 1.
Figure 4:
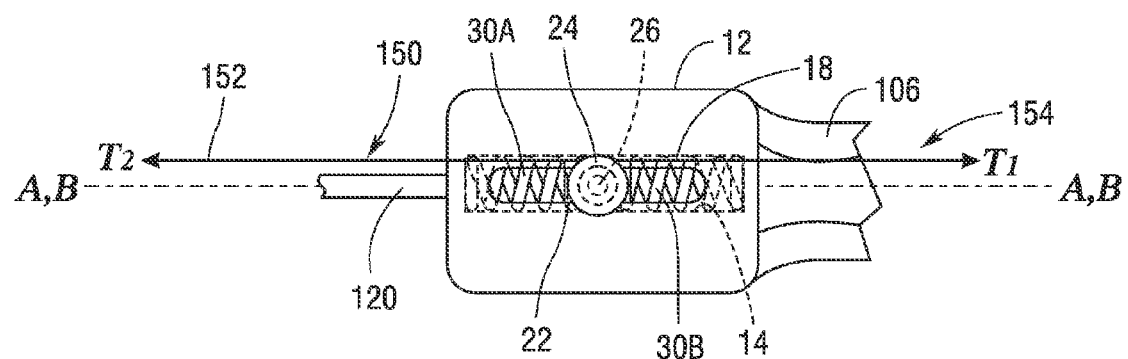
FIG. 4 is a bottom view of a portion of the handle assembly of FIGS. 1-3.

As can be most particularly seen in FIGS. 1 and 3, the suture tensioning device 10 may further comprise a movable tensioning member 20 that may comprise, for example, a movable mounting block 22 that has a tensioning spool 24 attached thereto or otherwise protruding therefrom. The mounting block 22 may be movably mounted within the axial passage 14 in the housing 12 such that it can axially move therein in the proximal direction "PD" and the distal direction "DD". See FIG. 5. The tensioning spool 24 may be rotatably affixed to the mounting block 22 by a shaft 26 that protrudes through an axial slot 18 provided in the housing 12. In other embodiments, the tensioning spool 24 may be rigidly affixed to the mounting block 22 and, in still other embodiments, for example, the tensioning spool 24 may be omitted such that only shaft 26 protrudes out through the axial slot 18. In other embodiments, the shaft 26 and mounting block 22 may comprise an integral component. In various embodiments, the mounting block 22 is centrally disposed between a first resilient member 30A and a second resilient member 30B. In various embodiments, members 30A and 30B may, for example, each comprise a coil spring as shown. As will be discussed in further detail below, the coil springs 30A and 30B may be substantially identical (i.e., they have the same size and spring constant) or in alternative embodiments, the coil springs 30A and 30B are not substantially identical.

Figure 5:
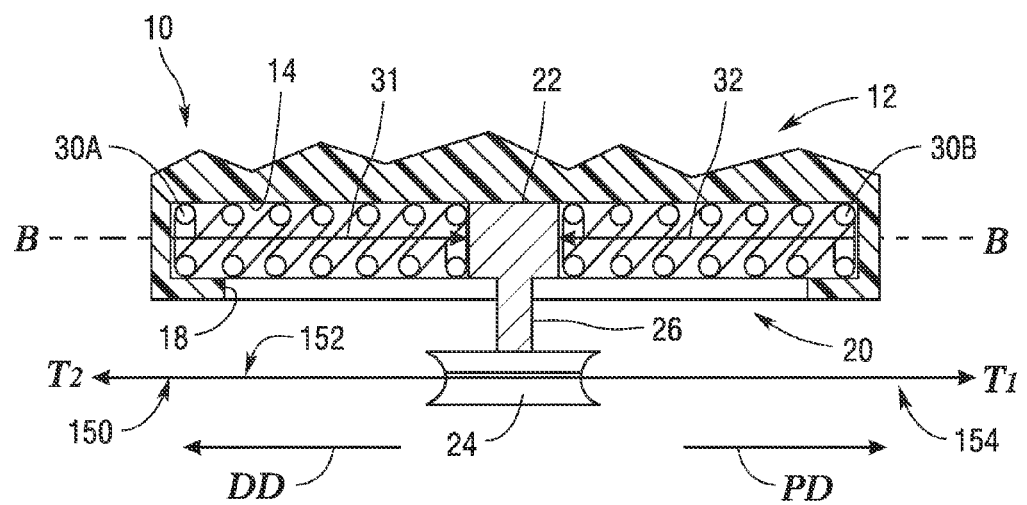
FIG. 5 is an enlarged cross-sectional view of a suture tensioning device of various embodiments of the present invention.

Operation of various embodiments of the suture tensioning device 10 may be understood from reference to FIG. 5. In mechanics and physics, Hooke's law of elasticity is an approximation that states that the amount by which a material body is deformed (the strain) is linearly related to the force causing the deformation (the stress). With respect to springs, such relationship is represented by the following equation:

$$F = kX$$

Where:

X is the distance that the spring has been stretched or compressed away from the equilibrium position, which is the position where the spring would naturally come to rest;

F is the restoring force exerted by the material; and k is the force constant or spring constant. The constant has units of force per unit length.

Returning to FIG. 5, as can be seen in that Figure, the suture 150 is wound or wrapped around the tensioning spool 24 at least one time or more than one time such that a distal portion 152 of the suture 150 extends to the stitch inside the patient and a proximal portion 154 of the suture 150 is outside of the patient wherein it may be grasped by the surgeon. In alternative embodiments, the spool 24 may be provided with a retention notch (not shown) into which a portion of the suture may be inserted to temporarily affix the suture to the spool 24. Prior to any tension being applied to the suture 150, the mounting block 22 is centrally disposed between the biasing members 30A and 30B. The first resilient member 30A and the second resilient member 30B may be substantially uncompressed or one resilient member may be in compression while the other resilient member is uncompressed or one resilient member may be in compression while the other one is in tension. T1 represents the amount of tension applied to the proximal portion 152 of the suture 150 by the surgeon and ultimately to the stitch (i.e., the distal end of the suture 150 that is anchored to the tissue, organ, etc.). The first resilient member 30A applies a first resistive force 31 to the mounting block 22 in the proximal direction "PD" and the second resilient member 30B applies a second resistive force 32 to the mounting block 22 in the distal direction "DD". Thus:

$$T2+Kx=T1$$

$$T2=T1-kX$$

Therefore: $T2 \ll T1$

Thus, the first and second resilient members 30A and 30B enable the surgeon to control the amount of tension ultimately applied to the anchored end of the suture 150. In various embodiments, the first and second resilient members 30A and 30B may be the same size. However, in alternative embodiments, the first and second resilient members are not the same size. After the desired amount of tension has been applied to the suture 150, the suture locking device is fired to install the suture knotting element as described in the aforementioned published U.S. Patent Application.

Figure 7:
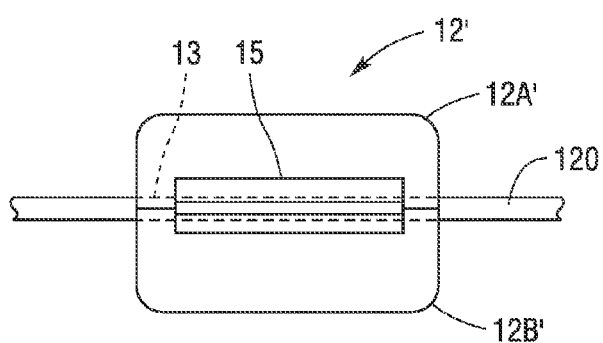
FIG. 7 is a top view of the suture tensioning device embodiment of FIG. 6.
Figure 6:
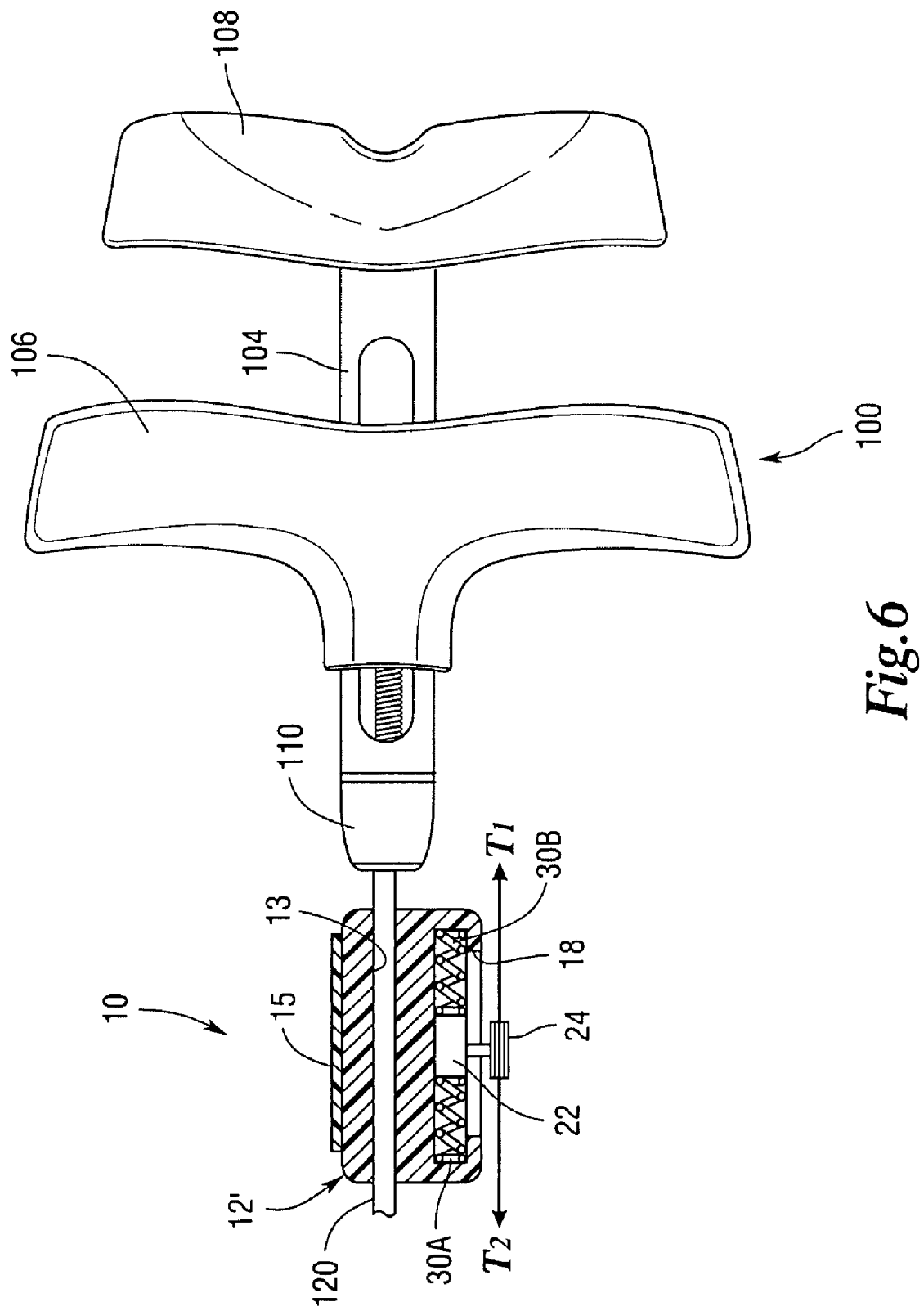
FIG. 6 is a side view of a handle assembly of a suturing device for delivering a suture to a surgical site and another suture tensioning device embodiment of the present invention.

FIGS. 6 and 7 illustrate another suture tensioning device 10' that is substantially similar to the tensioning device 10 described above except that the housing 12' is separate and apart from the grip portion 106. Thus, as can be seen in that Figure, the housing 12' may be fabricated in two pieces 12A' and 12B' that may be hinged together by hinge 15 or otherwise may be releasably coupled together. When coupled together, a lumen 13 is formed therein that is sized to lock onto catheter 120 as shown. The suture tensioning device 10' otherwise operates the same as the tensioning device 10 described above. In use, the surgeon may support the housing 12' on the catheter 120. In other embodiments, the housing 12' may be configured to retaining mate with the outer clamp 110 and/or body portion 104.

Figure 8:
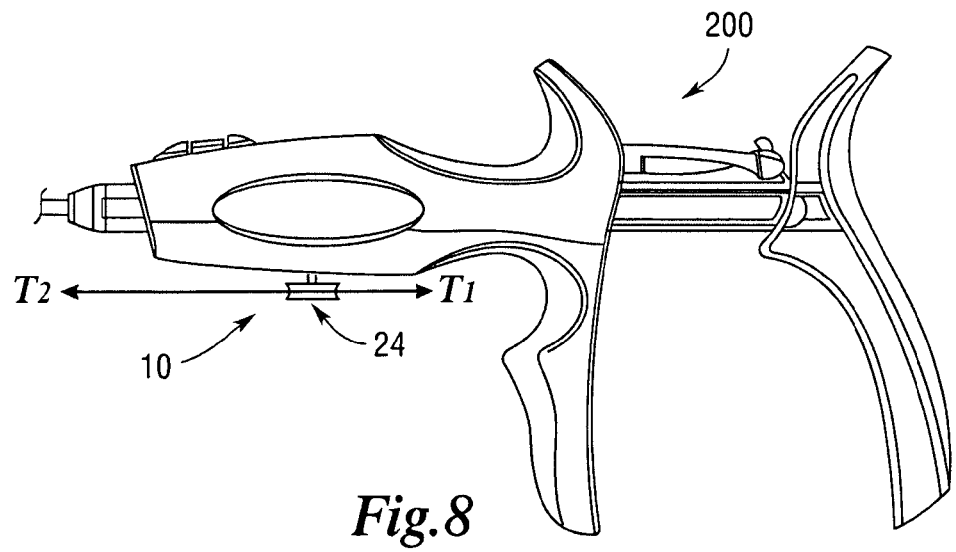
FIG. 8 is a side view of a handle assembly of another suturing device for delivering a suture to a surgical site with another suture tensioning device embodiment of the present invention incorporated therein.
Figure 9:
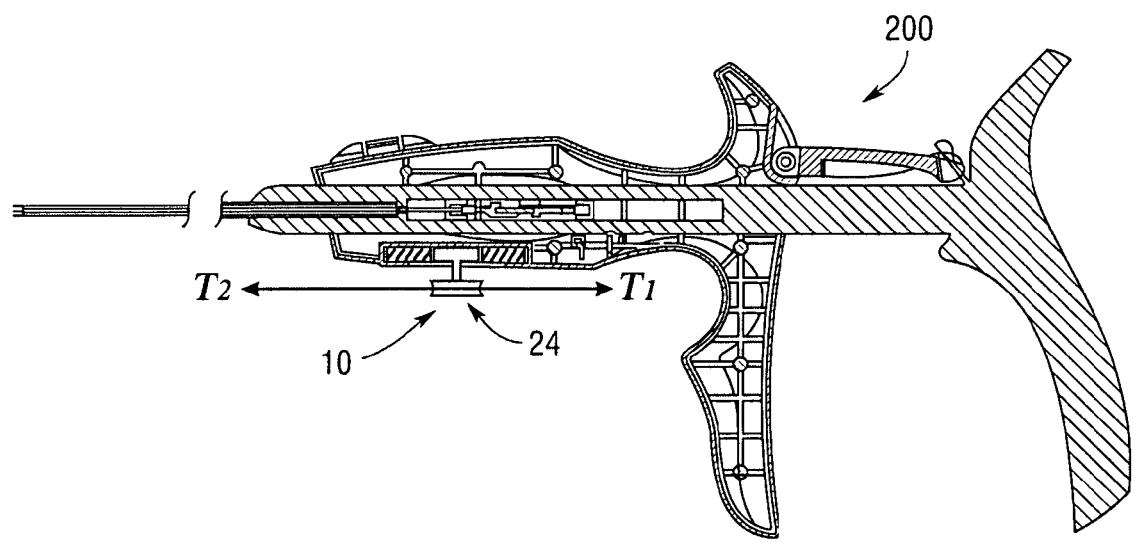
FIG. 9 is a cross-sectional view of the handle assembly of FIG. 8.
Figure 10:
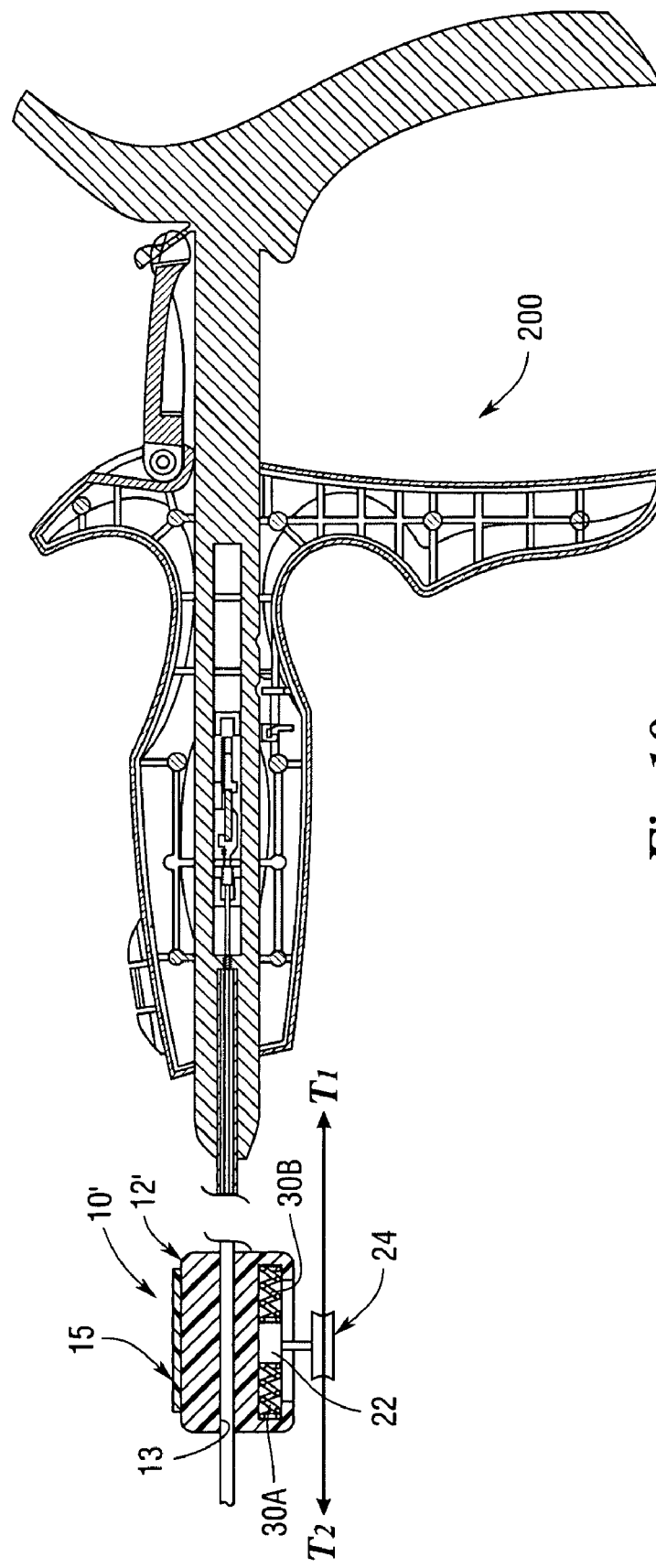
FIG. 10 is a cross-sectional view of a handle assembly of another suturing device for delivering a suture to a surgical site and another suture tensioning embodiment of the present invention.

FIGS. 8 and 9 illustrate the incorporation of a suture tensioning device 10 of an embodiment of the present invention into a known handle assembly 200 for of a suturing device for delivering a suture to a surgical site. FIG. 10 illustrates use of a suture tensioning device 10' embodiment of the present invention used in connection with the handle assembly 200.

The person of ordinary skill in the art will appreciate that the devices 10, 10' may be used in connection with the handle assembly 200 in the same manners as were described above.

Figure 11:
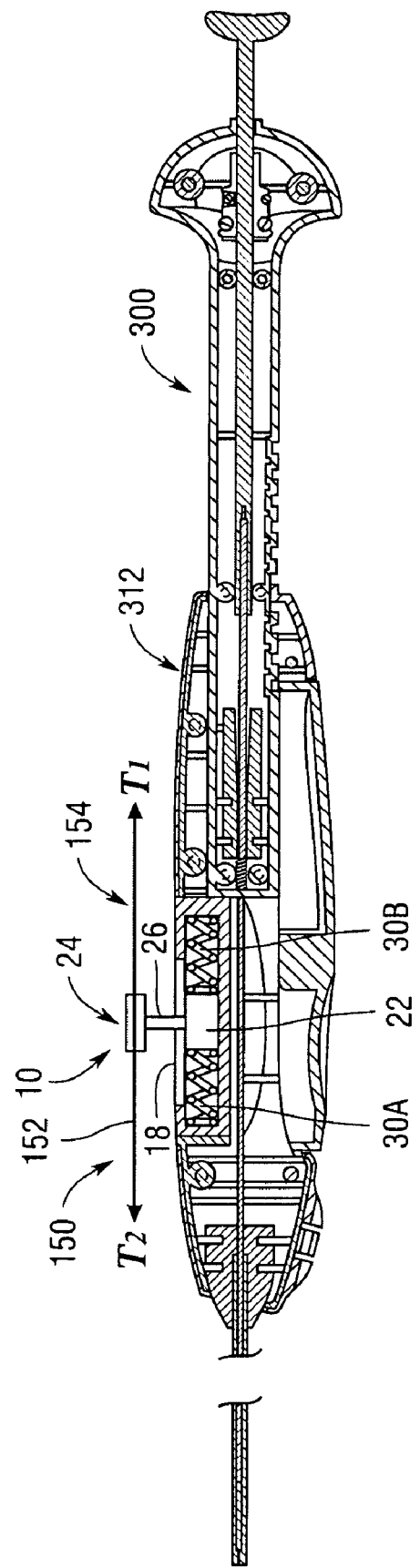
FIG. 11 is a side view of a handle assembly of another suturing device for delivering a suture to a surgical site with another suture tensioning device embodiment of the present invention incorporated therein.
Figure 12:
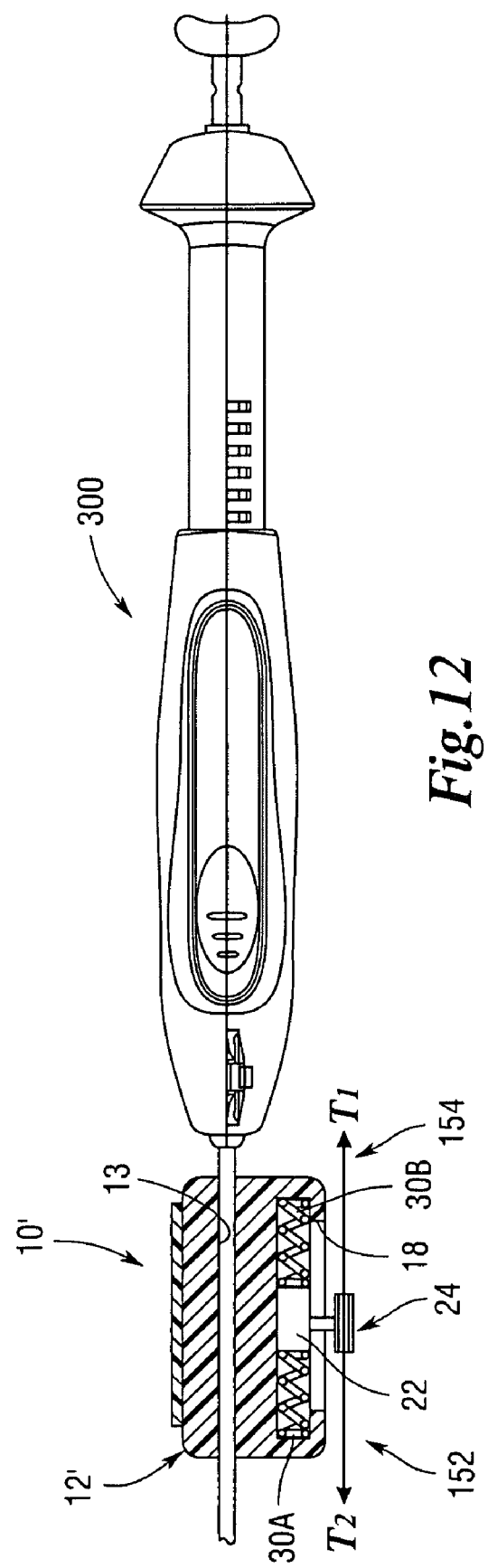
FIG. 12 is a top view of a handle assembly of another suturing device for delivering a suture to a surgical site with another suture tensioning device embodiment of the present shown in cross-section.

FIG. 11 illustrates the incorporation of a suture tensioning device 10 of an embodiment of the present invention into another known handle assembly 300 for a suturing device for applying suture anchors. Such handle assembly 300 may be similar in construction and operation to those handle assemblies disclosed in U.S. Patent Publication No. 2008/0103527 A1 to David T. Martin et al., entitled "Flexible Endoscopic Suture Anchor", filed Oct. 27, 2006 and pending co-owned U.S. patent application Ser. No. 11/796,035 to David Stefanchik et al., entitled "Surgical Suturing Apparatus", filed Apr. 26, 2007, the disclosures of each said application being herein incorporated by reference in their respective entireties. FIG. 12 illustrates use of a suture tensioning device 10' embodiment of the present invention used in connection with the handle assembly 300. The person of ordinary skill in the art will appreciate that the devices 10, 10' may be used in connection with the handle assembly 300 in the same manners as were described above.

Figure 13:
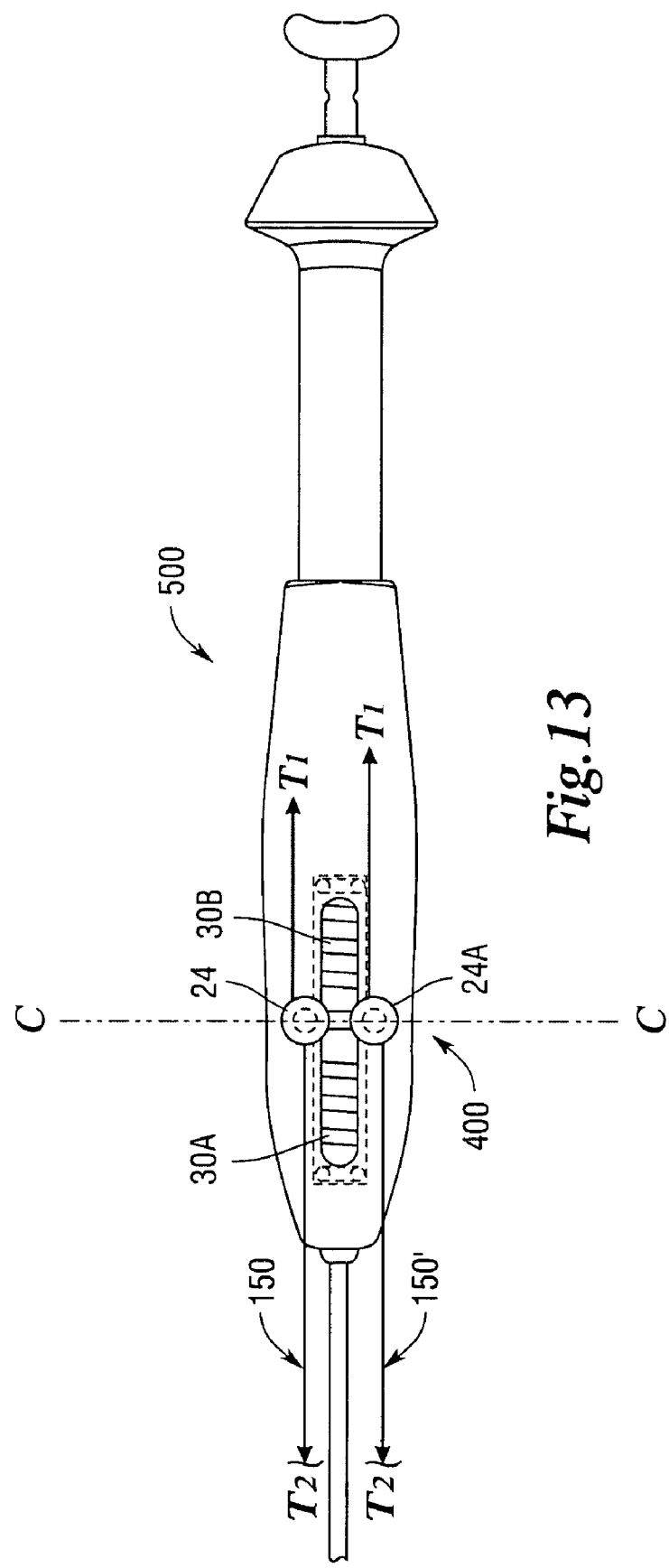
FIG. 13 is bottom view of another suturing device for delivering a suture to a surgical site with another suture tensioning device embodiment of the present invention incorporated therein.
Figure 14:
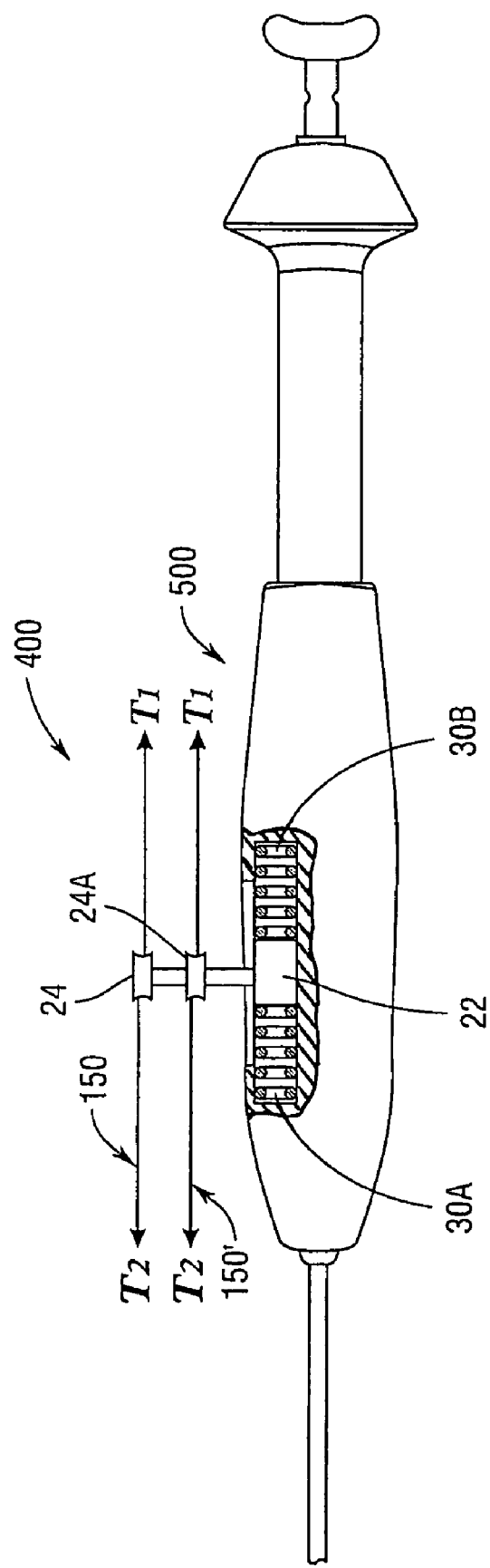
FIG. 14 is a side view of another suturing device for delivering a suture to a surgical site with another suture tensioning device embodiment of the present invention incorporated therein.

FIGS. 13 and 14 illustrate use of a suture tensioning device 400 embodiment of the present invention that may be effectively used to apply tension to two or more sutures 150 when employing a suture knotting and anchor applying device 500 of the type disclosed in published U.S. Patent Application Publication No. US 2007/0270889. As can be seen in those Figures, two spools 24 and 24A are mounted to the mounting block 22 to facilitate receipt of two separate sutures 150 and 150'. That is, suture 150 may be wrapped around spool 24 and suture 150' may be wrapped around spool 24A. In FIG. 13, the spools 24, 24A are essentially parallel to each other. That is, the spools 24, 24A are aligned along a transverse axis C-C that is substantially transverse to the sutures 150, 150'. In FIG. 14, the spools 24, 24A are coaxially aligned in a "stacked" arrangement along a vertically extending axis D-D. The suture tensioning device 400 may be used in connection with the knotting and anchor applying device 500 in the same manners as described above. Such "parallel" and "stacked" arrangements may also be successfully employed with the devices 10' described above. In addition, although use of two spools 24, 24A have been depicted, more than two spools could conceivably be employed to match the numbers of sutures.

Other embodiments of the present invention comprise a suture tension indication device 600 for indicating when excessive tension has been applied to a suture prior to firing the suture knotting device. While the various embodiments of the suture tension indicating device 600 may be incorporated into any of the suture handle arrangements referenced herein, FIGS. 15 and 16 depict a suture locking device 610 of the type described in U.S. Patent Application Publication No. US2007/0270907 with suture tension indication embodiment 600 of the present invention incorporated therein.

Figure 15:
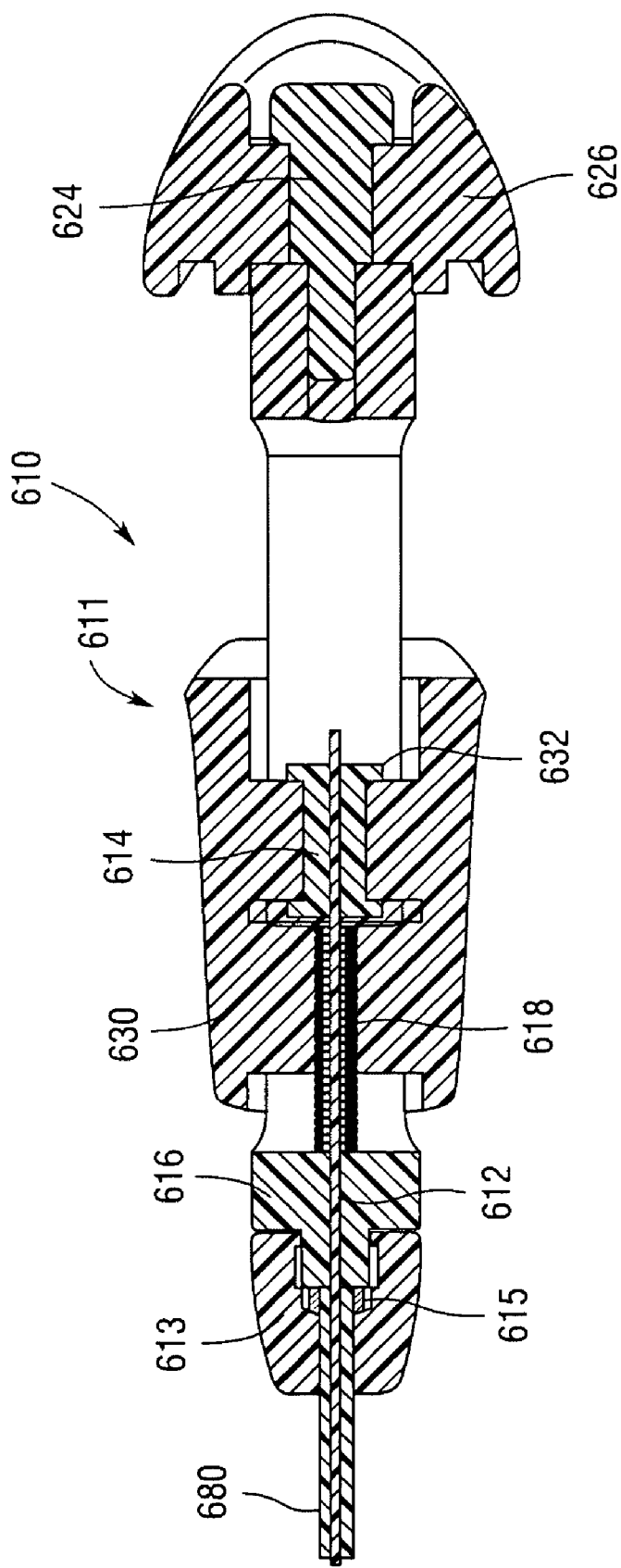
FIG. 15 is a cross-section of another handle assembly that may be employed with various embodiments of the present invention.
Figure 16:
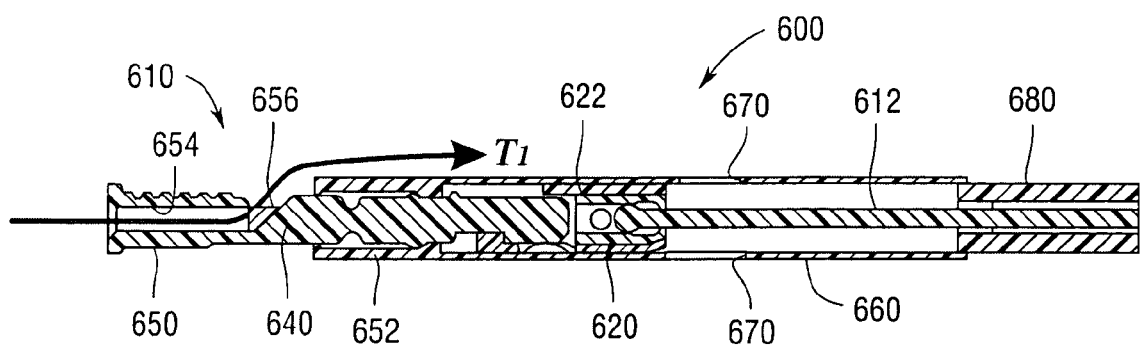
FIG. 16 is a cross-sectional view of a suture locking device embodiment of the present invention, showing the device threaded with suture material prior to firing.

FIG. 15 illustrates the proximal end of a catheter 680 and an exemplary handle 611 for deploying a knotting element from suture locking device 610. Handle 611 may be attached at the proximal end of drive cable 612 for applying tension to the cable. Handle 611 may comprise a longitudinal body portion 616, as well as a grip portion 630 for engaging the surgeon's fingers during operation of device 610. A thumb guide 626 may be located at the proximal end of handle 611. The distal end of handle 611 may include an outer clamp 613 having a center bore for passage of catheter 680. A ring 615 may be welded to the proximal end of catheter 680 and retained between clamp 613 and handle body 616 to secure the catheter 680. Drive cable 612 may extend proximally beyond clamp 613 and catheter 680 into a center bore 632 of handle body 616. A retaining member 614 may be longitudinally disposed in bore 632 of handle body 616. Grip 630 may be attached to retaining member 614 to move the retaining member within handle body 616 in response to pressure applied to the grip by the surgeon.

As can be further seen in FIG. 15, drive cable 612 extends into a center bore within a retaining member 614 located in a handle 611. The proximal end of drive cable 612 may be secured within retaining member 614 by an attachment mechanism, such as, for example, a piece of metal tubing crimped to the end of the cable. Drive cable 612 may be locked within retaining member 614 so as to move with the retaining member 614 along the longitudinal axis of handle body 616. A resilient member 618 may extend about drive cable 612 between the proximal end of handle body 616 and retaining member 614. Resilient member 618 serves to bias cable connector 620 into a proximal position within adaptor 622. See FIGS. 15 and 16. An attachment mechanism 624 is lodged in the proximal end of handle body 616 to attach thumb guide 626 to the handle body, and to allow for rotation of the guide relative to the handle body. Tension is applied to drive cable 612 by pulling proximally on grip 630. As grip 630 moves proximally, retaining member 614 moves proximally within bore 632 of handle body 616, due to the connection between the grip and retaining member. As retaining member 614 moves proximally, the length of drive cable 612 is pulled proximally, increasing the tension on the cable. The increased tension on drive cable 612 is transferred to launching member 640 via the interconnection between cable connector 620, adaptor 622, and launching member 640. Handle body bore 632 is sized to allow drive cable 612 to be pulled a sufficient distance to pull inner locking member 650 into outer locking member 652 as well as separate the knotting element from launching member 640.

To deploy a knotting element from suture locking device 610, the device is introduced into the working channel of an externalized endoscope in an initial, unfired position. Suture locking device 610 is advanced through the working channel of the endoscope until inner and outer locking members 650, 652 are visible beyond the distal end of the scope. To enable the surgeon to ascertain whether excessive tension has been applied to the suture 150, the suture locking device 610 is advanced out of the working channel at least until the indicator windows 670 are viewable with a camera as will be discussed in further detail below. Suture material 150 that has been externalized out the patient's mouth (or other orifice or incision) is threaded into the distal end of inner locking member 650. The suture material is passed through bore 654 of inner locking member 650 and out through opening 656 of launching member 640.

Following threading of suture material 150 into device 610, the surgeon reintroduces the endoscope into the patient, and advances the scope to the suture site using the suture strands as a guide. In-line tension "T1" is maintained on suture material 150 while device 610 is passed towards the suture site by holding the externalized ends of the suture material 150. During this process, there is a risk that the surgeon may apply excessive tension to the suture material 150 prior to firing the device 610. Accordingly, to provide the surgeon with an indication that excessive tension is being applied to the suture material 150, at least one indication window 670 is provided through the housing 660. The windows 670 are located relative to the adapter 622 in an unfired position such that when too much tension is applied to the suture 150, the suture will cause the launching member 640 and adapter 622 to move proximally in the housing 660. When the distal end of the adapter 622 becomes visible through the windows 670, the surgeon knows that excessive tension is being applied to the suture material 150. The surgeon may view the indicator windows 670 by the video camera (not shown) inserted through the endoscope (not shown). To assist the surgeon in detecting the proximal end of the adapter, the adapter may be provided in one or more bright colors.

As grip 614 is drawn proximally, drive cable 612 is pulled proximally through handle 611, catheter 680 and housing 660. The movement of drive cable 612 applies tension to adaptor 622, which in turn pulls launching member 640 proximally. As launching member 640 moves proximally along the device axis, inner locking member 650 is drawn into outer locking member 652 to lock the suture material 150 therebetween.

Figure 17:
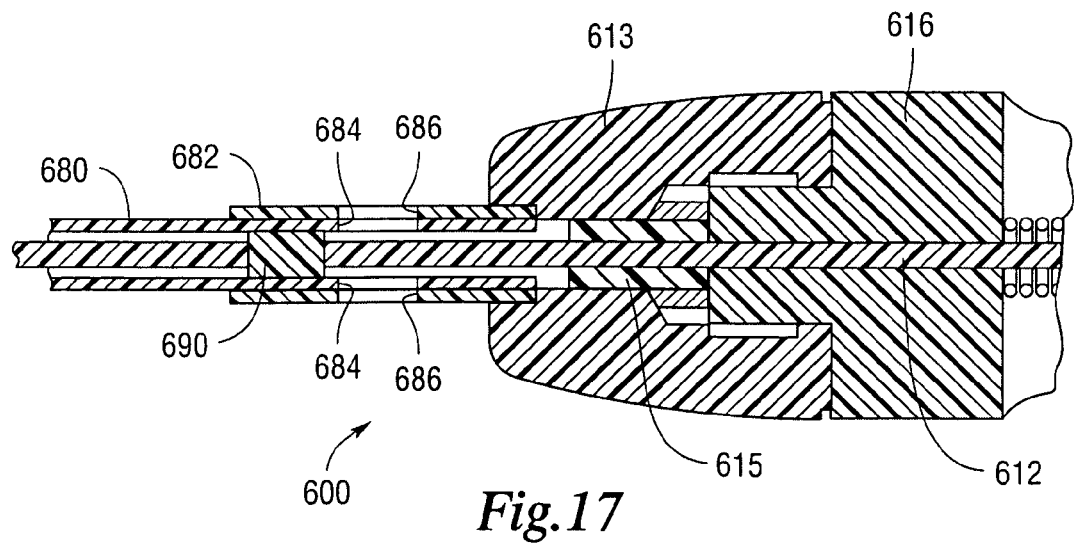
FIG. 17 is a cross-sectional view of a portion of another handle assembly embodiment of the present invention.

An alternative suture tension indication device 600' is depicted in FIG. 17. As can be seen in that Fig., a housing segment 682 is coupled to the outer clamp 613 or is otherwise supported adjacent to the handle, and extends around a portion of the catheter 680. In this embodiment, an indicator block 690 is attached to the drive cable 612 for movement within the catheter 680. At least one indicator window 684 is provided through the catheter 680 that is aligned with a corresponding window 686 in the housing 682 so that the indicator block 690 is viewable therethrough when excessive tension has been applied to the suture material 150 (not shown in FIG. 18). In particular, the windows 684, 686 are so located relative to the distal end of the indicator block 690 such that when a desired amount of tension is applied to the suture material, the indicator block 690 is not viewable through the windows 684, 686, yet when an excessive amount of tension is applied to the suture material, the drive cable 612 and indicator block 690 move proximally to a position wherein the surgeon can view the indicator block through those windows 684, 686. The suture locking device used with this embodiment may be identical to the suture locking device 610 described above —so that the surgeon would be able to detect when excessive tension has been applied to the suture material in two places (distally and proximally), or the device 600' may be used in connection with a suture locking device of the type disclosed in U.S. Patent Publication No. US2007/0270907.

As can be readily appreciated from the foregoing, the various embodiments of the present invention described above represent a vast improvement over prior devices and methods used to deliver and install sutures and/or apply an appropriate amount of tension to sutures as they are installed by the surgeon. The unique and novel features of the present invention may be effectively incorporated into a host of different known suturing devices that are used to deliver and/or install sutures through a natural orifice in the patient and thereby avoid several disadvantages associated with other conventional surgical methods and procedures that require incisions to be made into the abdomen. While the some embodiments of the present invention may be effectively incorporated into the handles of existing suturing devices, other embodiments may be separate from the handle assemblies and may be used in connection with several different types of suturing devices.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device can be reconditioned for reuse after at least one use. Reconditioning can include a combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A suture tensioning device, comprising:
    a housing a lumen extending therethrough that defines a longitudinal axis; and
    a movable tensioning member comprising:
        a mounting block constrained to move axially within an axial passage in said housing along a second axis that is laterally offset from said longitudinal axis; and
        a shaft portion protruding from said mounting block configured to have a portion of a suture wound therearound such that a distal portion of the suture extends in a distal direction from the movable tensioning member to be anchored to tissue and a proximal portion of the suture protrudes from the movable tensioning member to have tension applied thereto;
        a spool attached to said shaft portion such that the portion of the suture may be wound therearound;
    a first resilient member for applying a first resistive force to said movable tensioning member in a first direction, wherein said first resilient member comprises a first coil spring; and
    a second resilient member applying a second resistive force to said movable tensioning member in a second direction opposite to said first direction, wherein said second resilient member comprises a second coil spring; and wherein said mounting block is centrally disposed between said first and second resilient members.

2. The suture tensioning device of claim 1 wherein said first coil spring has a first spring constant and wherein said second coil spring has a second spring constant that is substantially equal to said first spring constant.

3. The suture tensioning device of claim 1 wherein said housing comprises a portion of a handle of a suturing device configured to deliver a suture to a surgical site.

4. The suture tensioning device of claim 1 wherein said lumen is to receive a catheter of a suturing device.

5. The suture tensioning device of claim 4 further comprising:
    a suture locking device comprising:
    an indicator housing member on the catheter;
    a first locking element operably supported within said indicator housing member and oriented to permit said suture to extend therethrough;
    a second locking element supported relative to said first locking element and configured to retainingly engage said first locking element upon application of a firing motion to said first locking element to thereby cause a portion of the suture extending through said first locking element to be locked between said first and second locking elements; and
    an indicator member supported within said indicator housing and configured to only be viewable through an external wall thereof when an excessive amount of tension has been applied to the suture prior to applying the firing motion to said first locking member.

6. The suture tensioning device of claim 5 further comprising at least one indicator window in said external wall of said indicator housing such that when an excessive amount of tension has been applied to the suture prior to the application of said firing motion, said indicator member is viewable through said at least one indicator window.

7. The suture tensioning device of claim 5, further comprising:
    a handle; and
    a drive cable operably coupled to said handle and said first locking element for applying said firing motion thereto.

8. The suture tensioning device of claim 7 wherein said drive cable is coupled to said indicator member and wherein said indicator member operably interfaces with said first locking element.

9. The suture tensioning device of claim 7 wherein said drive cable extends through the catheter extending between said handle and said housing member and wherein said suture tensioning device further comprises a second indicator member interfacing with said drive cable and configured to only be viewable through said catheter adjacent said handle when an excessive amount of tension has been applied to the suture prior to applying the firing motion to said first locking member.

10. The suture tensioning device of claim 6 wherein said indicator member has a color that is readily viewable through said at least one indicator window.

11. A suture application and management kit, comprising:
   a suturing device configured to deliver a suture to a surgical site; and
   a suture tensioning device of claim 1.

12. The suture application and management kit of claim 11 wherein the suturing device includes at least one end effector configured to apply at least one fastener to tissue, the suture being coupled to the at least one fastener.

13. The suture application and management kit of claim 11 wherein the suture tensioning device is coupled to the suturing device configured to deliver a suture to a surgical site.

14. A method for processing an instrument for surgery, the method comprising: obtaining the suture tensioning device of claim 1;
   sterilizing the suture tensioning device; and
   storing the suture tensioning device in a sterile container.

* * * * *